US010239953B2

(12) United States Patent
Declerck et al.

(10) Patent No.: US 10,239,953 B2
(45) Date of Patent: Mar. 26, 2019

(54) DUAL TARGETING OF TAFI AND PAI-1

(71) Applicants: KATHOLIEKE UNIVERSITEIT LEUVEN, Leuven (BE); INSERM (Institut National de la Santé et de la Recherche Médicale), Paris (FR); Université de Caen Basse Normandie, Caen (FR); Centre Hospitalier Universitaire de Caen, Caen (FR)

(72) Inventors: Paul Declerck, Leuven (BE); Simon De Meyer, Leuven (BE); Nick Geukens, Leuven (BE); Ann Gils, Leuven (BE); Marina Rubio, Caen (FR); Denis Vivien, Caen (FR); Tine Wyseure, Leuven (BE)

(73) Assignees: KATHOLIEKE UNIVERSITEIT LEUVEN, Leuven (BE); INSERM (INSTITUT NATIONAL DE LA SANTÉ ET DE LA RECHERCHE MÉDICALE), Paris (FR); UNIVERSITÉ DE CAEN BASSE NORMANDIE, Caen (FR); CENTRE HOSPITALIER UNVIERSITAIRE DE CAEN, Caen (FR)

( * ) Notice: Subject to any disclaimer, the term of this patent is extended or adjusted under 35 U.S.C. 154(b) by 98 days.

(21) Appl. No.: 15/117,027

(22) PCT Filed: Feb. 9, 2015

(86) PCT No.: PCT/EP2015/052624
§ 371 (c)(1),
(2) Date: Aug. 5, 2016

(87) PCT Pub. No.: WO2015/118147
PCT Pub. Date: Aug. 13, 2015

(65) Prior Publication Data
US 2016/0347859 A1 Dec. 1, 2016
US 2017/0253664 A2 Sep. 7, 2017

Related U.S. Application Data
(60) Provisional application No. 61/937,323, filed on Feb. 7, 2014.

(30) Foreign Application Priority Data
Mar. 19, 2014 (GB) .................................. 1404879.7
Mar. 19, 2014 (GB) .................................. 1404880.5
Jul. 4, 2014 (GB) .................................. 1411979.6
Dec. 18, 2014 (GB) .................................. 1422609.6

(51) Int. Cl.
*A61K 39/395* (2006.01)
*C07K 16/38* (2006.01)
*A61K 39/00* (2006.01)

(52) U.S. Cl.
CPC ........ *C07K 16/38* (2013.01); *A61K 2039/505* (2013.01); *C07K 2317/24* (2013.01); *C07K 2317/31* (2013.01); *C07K 2317/565* (2013.01); *C07K 2317/76* (2013.01)

(58) Field of Classification Search
None
See application file for complete search history.

(56) References Cited

FOREIGN PATENT DOCUMENTS

WO    1990006133 A1    6/1990
WO    WO 9823151 A1 *  6/1998   ........... A61K 9/7023

OTHER PUBLICATIONS

Develter et al., J Thromb Haemost. Nov. 2008;6(11):1884-91. doi: 10.1111/j.1538-7836.2008.03137.x. Epub Aug. 22, 2008.*
Vercauteren et al., Blood. Apr. 28, 2011;117(17):4615-22. doi: 10.1182/blood-2010-08-303677. Epub Feb. 22, 2011.*
Debrock et al., "Neutralization of Plasminogen Activator Inhibitor-1 Inhibitory Properties: Identification of Two Different Mechanisms," Biochimica et Biophysica Acta, 1997, pp. 257-266, vol. 1337.
Develter et al., "Bispecific Targeting of Thrombin Activatable Fibrinolysis Inhibitor and Plasminogen Activator Inhibitor-1 by a Heterodimer Diabody," Journal of Thrombosis and Haemostasis, 2008, pp. 1884-1891, vol. 6.
Fernandez-Cadenas et al., "Influence of Thrombin-Activatable Fibrinolysis Inhibitor and Plasminogen Activator Inhibitor-1 Gene Polymorphisms on Tissue-Type Plasminogen Activator-Induced Recanalization in Ischemic Stroke Patients," Journal of Thrombosis and Haemostasis, 2007, pp. 1862-1868, vol. 5.
Great Britain Search Report for corresponding Great Britain Application No. 1404879.7, dated Jan. 21, 2015.
Great Britain Search Report for corresponding Great Britain Application No. 1404880.5, dated Jan. 21, 2015.
Hillmayer et al., "Discovery of Novel Mechanisms and Molecular Targets for the Inhibition of Activated Thrombin Activatable Fibrinolysis Inhibitor," Journal of Thrombosis and Haemostasis, 2008, pp. 1892-1899, vol. 6.
International Preliminary Report on Patentability for corresponding International PCT Application No. PCT/EP2015/052624, dated Apr. 29, 2016.
International Search Report for corresponding International PCT Application No. PCT/EP2015/052624, dated May 4, 2015.
Klement al., "Hemostasis, Thrombosis, and Vascular Biology—A Novel Approach to Arterial Thrombolysis," Blood, Oct. 15, 1999, pp. 2735-2743, vol. 94, No. 8.

(Continued)

*Primary Examiner* — Michael Szperka
(74) *Attorney, Agent, or Firm* — Workman Nydegger

(57) ABSTRACT

Disclosed herein is a bispecific inhibitor for use in treating thrombotic disorders, such as acute thrombotic disorders like stroke and thromboembolism. The bispecific inhibitor is based on monoclonal antibodies targeting TAFI and PAI-1, and shows efficacy in the presence or the absence of plasminogen activators such as tissue-type plasminogen activator (tPA).

19 Claims, 11 Drawing Sheets
Specification includes a Sequence Listing.

(56) References Cited

OTHER PUBLICATIONS

Mutch et al., "Thrombus Lysis by uPA, scuPA and tPA is Regulated by Plasma TAFI," Journal of Thrombosis and Haemostasis, 2003, pp. 2000-2007, vol. 1.

Viutch et al., "TAFIa, PAI-1 and α2-Antiplasmin: Complementary Roles in Regulating Lysis of Thrombi and Plasma Clots," Journal of Thrombosis and Haemostasis, 2007, pp. 812-817, vol. 5.

Rijken et al., "New Insights into the Molecular Mechanisms of the Fibrinolytic System," Journal of Thrombosis and Haemostasis, 2009, pp. 4-13, vol. 7.

Saver, "Improving Reperfusion Therapy for Acute Ischaemic Stroke," Journal of Thrombosis and Haemostasis, 2011, pp. 333-343, vol. 9 (Suppl. 1).

Semeraro et al., "Monoclonal Antibodies Targeting the Antifibrinolytic Activity of Activated Thrombin-Activatable ribrinolysis Inhibitor but not the Anti-Inflammatory Activity on Osteopontin and C5a," Journal of Thrombosis and Haemostasis, 2013, pp. 2137-2147, vol. 11.

Van De Craen et al., "Characterization of a Panel of Monoclonal Antibodies Toward Mouse PAI-1 that Exert a Significant Profibrinolytic Effect in Vivo," Thrombosis Research, 2011, pp. 68-76, vol. 128.

Van Giezen et al., "The Fab-Fragment of a PAI-1 Inhibiting Antibody Reduces Thrombus Size and Restores Blood Flow in a Rat Model of Arterial Thrombosis," Thrombosis and Haemostasis, 1997, pp. 964-969, vol. 77, No. 5.

Verbeke et al., "Inhibition of Plasminogen Activator Inhibitor-1: Antibody Fragments and Their Unique Sequences as a Tool for the Development of Profibrinolytic Drugs," Journal of Thrombosis and Haemostasis, 2004, pp. 298-305, vol. 2.

Vercauteren et al., "Evaluation of the Profibrinolytic Properties of an Anti-TAFI Monoclonal Antibody in a Mouse Thromboembolism Model," Blood, Apr. 28, 2011, pp. 4615-4622, vol. 117, No. 17.

Vercauteren et al., "The Hyperhbrinolytic State of Mice with Combined Thrombin-Activatable Fibrinolysis Inhibitor (TAFI) and Plasminogen Activator Inhibitor-1 Gene Deficiency is Critically Dependent on TAFI Deficiency," Journal of Thrombosis and Haemostasis, 2012, pp. 2555-2562, vol. 10.

Wyseure et al., "Evaluation of the Profibrinolytic Properties of a Bispecific Antibody-Based Inhibitor Against Human and Mouse Thrombin-Activatable Fibrinolysis Inhibitor and Plasminogen Activator Inhibitor-1," Journal of Thrombosis and Haemostasis, 2013, pp. 2069-2071, vol. 11.

Wyseure et al., "Innovative Thrombolytic Strategy Using a Heterodimer Diabody Against TAFI and PAI-1 in Mouse Models of Thrombosis and Stroke," Blood, Feb. 19, 2015, pp. 1325-1332, vol. 125, No. 8.

\* cited by examiner

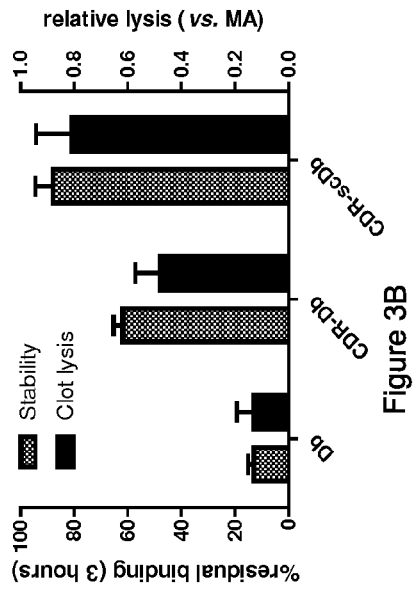
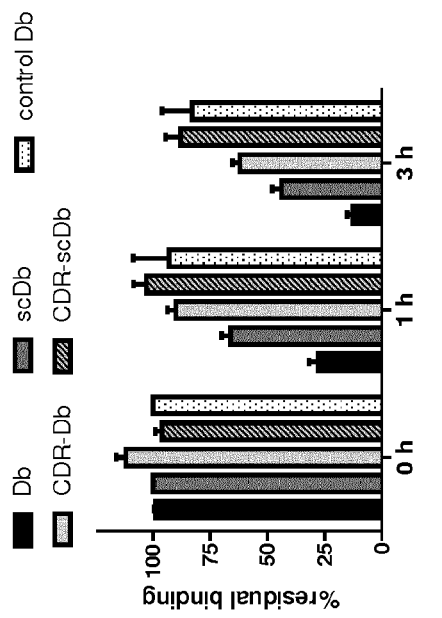
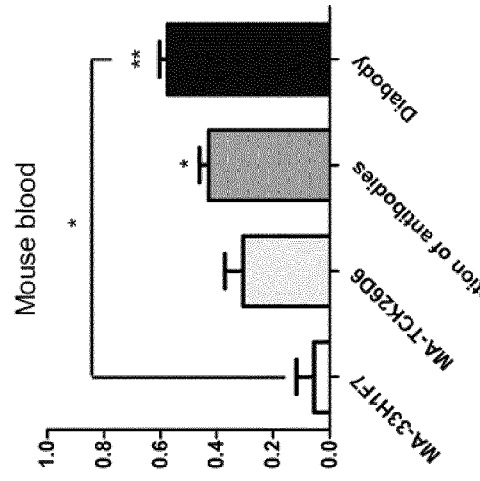
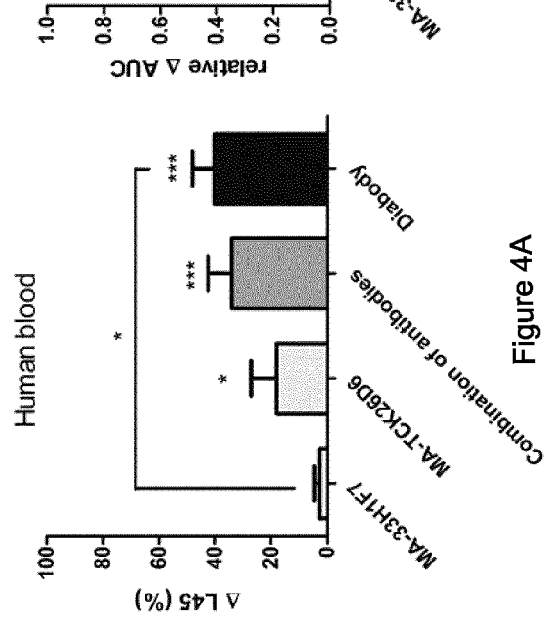
Figure 3A
Figure 3B
Figure 4A
Figure 4B

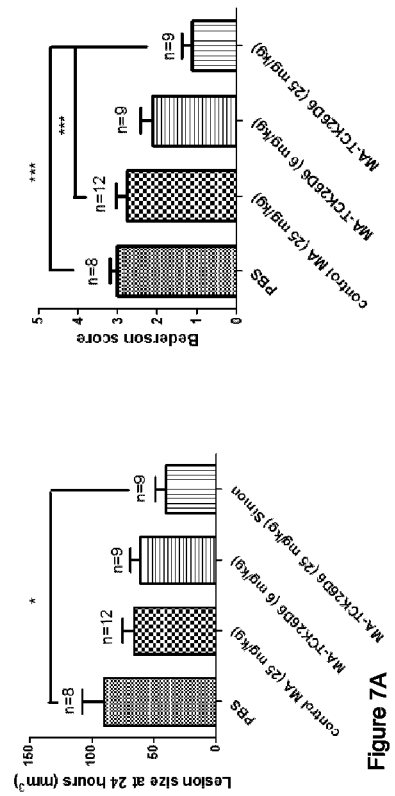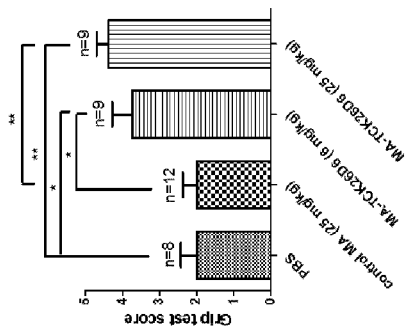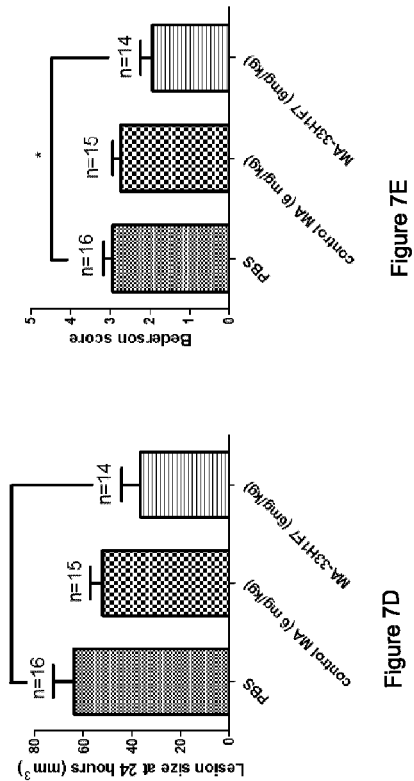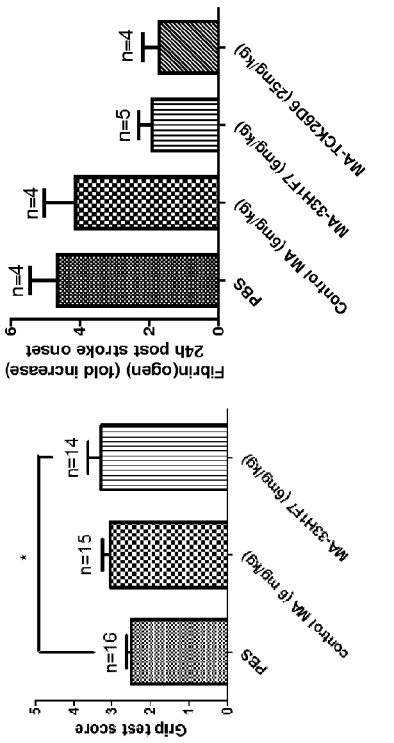

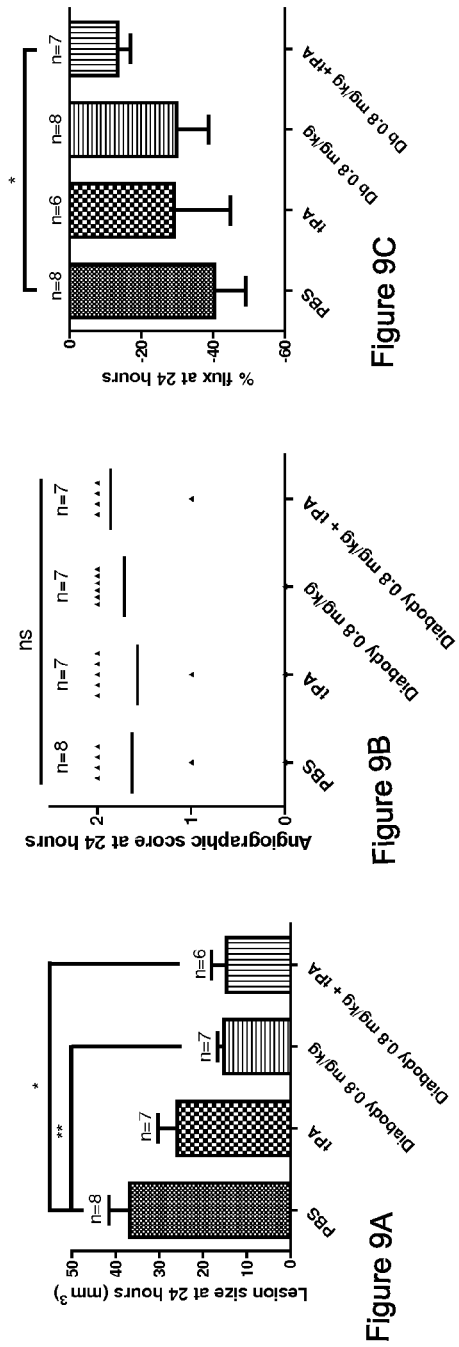
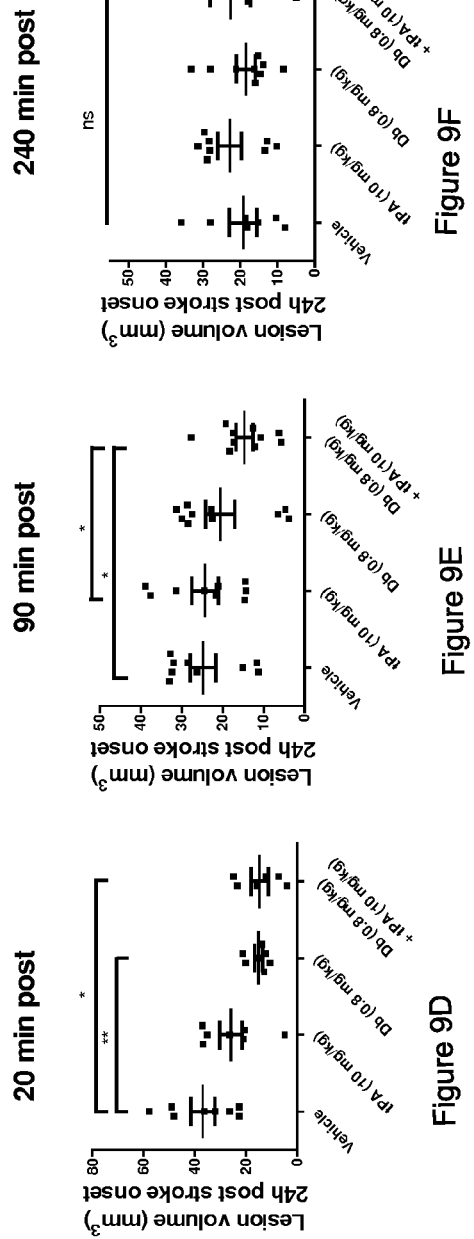

Figure 11A
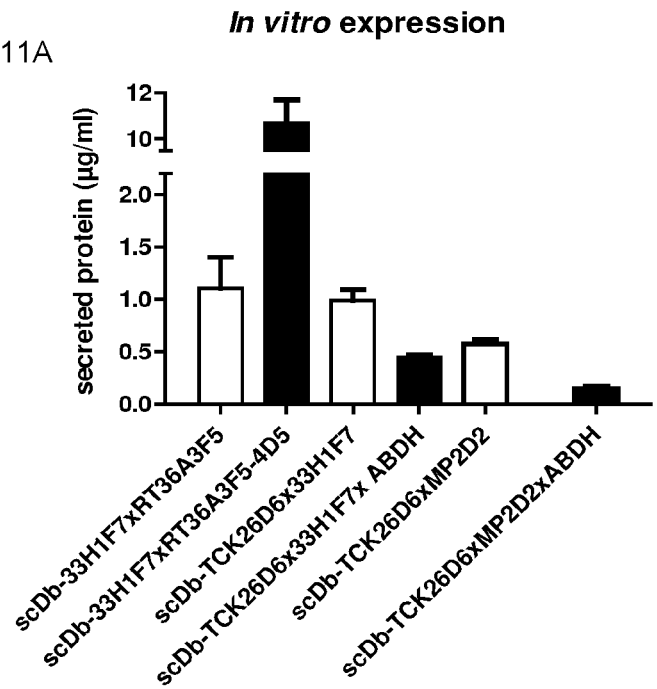
Figure 11B
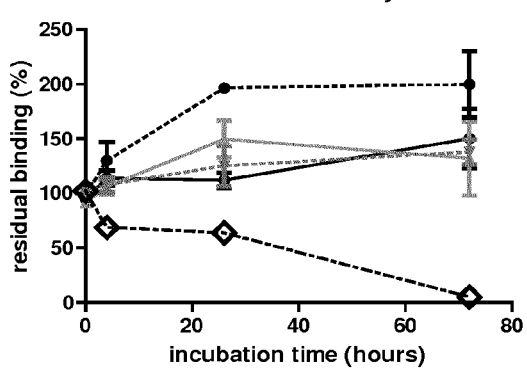
Figure 11C
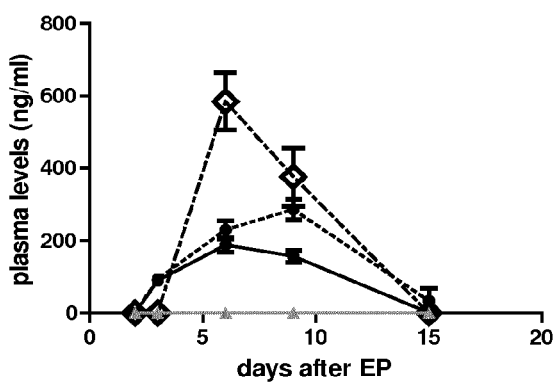

DUAL TARGETING OF TAFI AND PAI-1

FIELD OF INVENTION

The present invention relates generally to treatment and prevention of thrombotic disorders such as stroke and thromboembolism by dual inhibition of plasminogen activator inhibitor 1 (PAI-1) and Thrombin-Activatable Fibrinolysis Inhibitor (TAFI). The dual inhibition may be mediated by a bispecific antibody derivative that binds to both targets.

REFERENCE TO SEQUENCE LISTING SUBMITTED VIA EFS-WEB

This application includes an electronically submitted sequence listing in .pdf format. The .pdf file contains a sequence listing entitled "19893-18-Sequence_Listing.pdf" created on Aug. 5, 2016 and is 43 bytes in size. The sequence listing contained in this .pdf file is part of the specification and is hereby incorporated by reference herein in its entirety.

BACKGROUND

Following an acute cardiovascular accident, the only treatment currently available to recanalize an occluded blood vessel is systemic delivery of a high dose of plasminogen activators. While effective when administered soon after the event, plasminogen activators also cause debilitating side effects such as intracranial haemorrhage and neurotoxicity. In addition, successful restoration of blood flow is not guaranteed because of low recanalization and high reocclusion rates, even when high doses of plasminogen activators are administered [Saver J L. et al. (2011) J Thromb Haemost. 9 Suppl 1, 333-343]. Accordingly, there remains a need in the art for effective treatments of occluded blood vessels, for example by promoting fibrinolysis or thrombolysis.

One of the causes for thrombolytic failure is the presence of circulating inhibitors of fibrinolysis, such as Thrombin-Activatable Fibrinolysis Inhibitor (TAFT) and plasminogen activator inhibitor 1 (PAI-1) [Fernandez-Cadenas I et al. (2007) J Thromb Haemost. 5, 1862-1868]. Both molecules slow down the tissue type-plasminogen activator (tPA)-mediated formation of plasmin, the key enzyme in fibrinolysis, although through distinct mechanisms (as reviewed in Rijken D C & Lijnen H R (2009) J Thromb Haemost. 7, 4-13). TAFI, a 56 kDa proenzyme with a plasma level of 4-15 µg/ml, can be activated into TAFIa by thrombin, alone or in complex with thrombomodulin, or plasmin. Through its carboxypeptidase activity, TAFIa is able to cleave off C-terminal Lys residues exposed on partially degraded fibrin, which serve as a co-factor function in the tPA-mediated activation of plasminogen into plasmin. PAI-1 (45 kDa glycoprotein with a plasma level of 5-50 ng/ml and a concentration within platelets of 200 ng/ml) is the main inhibitor of tPA and belongs to the serine protease inhibitors (serpin) superfamily. The active form of PAI-1 can irreversibly neutralize the activity of tPA by forming a 1:1 stoichiometric covalent complex, accompanied by deformation of catalytic triad of the serine protease.

Given their complementary roles in inhibiting fibrinolysis, one approach to promoting fibrinolysis is dual inhibition of TAFI and PAI-1. Simultaneous targeting of TAFI and PAI-1 has been attempted in several studies. However, the results did not consistently indicate that dual inhibition of TAFI and PAI-1 improved thrombolysis as compared to single inhibition. In one study, complementary roles of TAFI and PAI-1, as well as a third molecule $\alpha_2$-AP, were characterized in tPA induced thrombolysis assays in the presence or absence of inhibitors of TAFI, PAI-1, and/or $\alpha_2$-AP [Mutch N J. et al. (2007) J Thromb Haemost. 5, 812-817]. Depending on the type of thrombus, the assays indicated either a role for all three molecules or a substantial contribution of $\alpha_2$-AP and TAFI, with a minor contribution from PAI-1. Similarly, single and double knockout studies in mice suggested that thrombolytic effects in certain assays were due to inhibition of TAFI rather than PAI-1 [Vercauteren E et al. (2012) J Thromb Haemost. 10, 2555-2562].

Notably, a dual targeting strategy based on bispecific antibody derivatives (diabodies) has shown promise. The diabody T12D11x33H1F7, based on monoclonal antibodies which bind TAFI and PAI-1, was shown to have a stimulating effect on fibrinolysis which exceeded the effect observed when its component monoclonal antibodies (MA) were tested separately. In addition, new monoclonal antibodies against TAFI and PAI-1 exhibit unique features. MA-RT36A3F5 and MA-TCK26D6 both inhibit mouse and rat TAFI, with each MA acting through distinct mechanisms: the former destabilizes TAFIa, whereas the latter impairs the plasmin-mediated activation of TAFI and also interferes with the interaction of TAFIa on fibrin [Hillmayer K et al. J (2008) Thromb Haemost. 6, 1892-1899; Vercauteren E et al. (2011) Blood 117, 4615-4622; Semeraro F, et al. (2013) J Thromb Haemost. 11, 2137-2147]. MA-33H1F7 and MA-MP2D2 inhibit mouse and rat PAI-1, by converting the active form into a substrate form of PAI-1 which is cleaved by tPA [Debrock S. & Declerck P J. (1997) Biochim Biophys Acta. 1337, 257-266; Van De Craen B. et al. (2011) Thromb Res. 128, 68-76]. In vivo studies have shown a beneficial effect of the above mentioned antibodies on the rate of survival and paralysis in mice after thromboembolic challenge [Vercauteren (2011) cited above, Van De Craen cited above]. Recently, the MA antibodies MA-33H1F7 and MA-TCK26D6 which specifically recognize the corresponding human antigens were adapted to make the bispecific antibody derivative Db-TCK26D6x33H1F7, and a strong profibrinolytic effect of the diabody was demonstrated in vitro [Wyseure T et al. (2013) J Thromb Haemost. 11, 2069-2071]. However, no dual targeting studies to date have conclusively demonstrated a role for inhibitors or diabodies in treating specific thrombotic disorders in vivo. In addition, no studies have provided evidence for viable treatments for thrombotic disorders based on inhibitors of fibrinolysis or thrombolysis as alternatives to plasminogen activators.

SUMMARY OF INVENTION

Described herein is the diabody Db-TCK26D6x33H1F7 for use in treating thrombotic disorders, such as stroke and thromboembolism. Db-TCK26D6x33H1F7 may be administered either before or after the onset of the thrombotic disorder, and moreover, may be administered in the presence or the absence of plasminogen activators such as tPA.

The present disclosure relates to a bispecific antibody derivative for use in treating an acute thrombotic disorder in a patient, comprising a first targeting domain that binds to Thrombin Activatable Fibrinolysis Inhibitor (TAFI) and comprises complementary determining regions (CDRs) represented by amino acid sequences that are at least 80% identical to each of CDR1H of SEQ ID NO:1, CDR2H of SEQ ID NO:2, CDR3H of SEQ ID NO:3, CDR1L of SEQ ID NO:4, CDR2L of SEQ ID NO:5, and CDR3L of SEQ ID NO:6; and a second targeting domain that binds to Plasminogen Activator Inhibitor-1 (PAI-1) and comprises complementary determining regions (CDRs) represented by amino acid sequences that are at least 80% identical to each of CDR1H of SEQ ID NO:7, CDR2H of SEQ ID NO:8, CDR3H of SEQ ID NO:9, CDR1L of SEQ ID NO:10, CDR2L of SEQ ID NO:11, and CDR3L of SEQ ID NO:12, wherein the bispecific antibody derivative is administered after onset of the acute thrombotic disorder.

In some embodiments, the amino acid sequences in the bispecific antibody derivatives are at least 80%, 85%, 90%, 95%, 99% or 100% identical to the amino acid sequences disclosed in SEQ ID NO:1-18. In some embodiments, the bispecific antibody derivative is for use in an acute thrombotic disorder that is at least one of acute ischemic stroke (AIS), middle cerebral artery occlusion (MCAo), thromboembolism, deep vein thrombosis, myocardial infarction (MI), pulmonary embolism, peripheral arterial disease, thrombosis of liver and/or kidneys, or catheter blockage. For example, the acute thrombotic disorder may be AIS. The acute thrombotic disorder may be MCAo.

In certain embodiments, the bispecific antibody derivative is administered between 0-15 hours after onset of symptoms of the acute thrombotic disorder. In some embodiments, the bispecific antibody derivative is administered up to 3 hours after onset of symptoms of the acute thrombotic disorder. In some embodiments, the bispecific antibody derivative is administered up to 4.5 hours after onset of symptoms of the acute thrombotic disorder. In some embodiments, the bispecific antibody derivative is administered up to 12 hours after onset of symptoms of the acute thrombotic disorder.

The bispecific antibody derivative may be administered without tPA. In some embodiments, the bispecific antibody derivative is administered without tPA during a time period of up to 90 minutes after the onset of the acute thrombotic disorder, for example, 0-90 minutes after onset.

In some embodiments, the bispecific antibody derivative is administered with tPA. For example, the bispecific antibody derivative may be administered 1 hour after administration of tPA.

In some embodiments, bispecific antibody derivative is for use in an acute thrombotic disorder that is characterized by presence of a fibrin-rich blood clot. The acute thrombotic disorder may be characterized by presence of a platelet-rich blood clot.

In certain embodiments, the bispecific antibody derivative is humanized.

A further aspect of the present disclosure relates to a bispecific antibody derivative for use in treating an acute thrombotic disorder in a patient, comprising a first targeting domain that binds to Thrombin Activatable Fibrinolysis Inhibitor (TAFI) and comprises a VH region represented by an amino acid sequence that is at least 80% identical to SEQ ID NO:13 and a VL region represented by an amino acid sequence that is at least 80% identical to SEQ ID NO:14; and a second targeting domain that binds to Plasminogen Activator Inhibitor-1 (PAI-1) and comprises a VH region represented by an amino acid sequence that is at least 80% identical to SEQ ID NO:15 and a VL region represented by an amino acid sequence that is at least 80% identical to SEQ ID NO:16, wherein the bispecific antibody derivative is administered after onset of the acute thrombotic disorder. In some embodiments, a bispecific antibody derivative for use in treating an acute thrombotic disorder in a patient, comprising a first domain represented by an amino acid sequence that is at least 80% identical to SEQ ID NO:17; and a second domain represented by an amino acid sequence that is at least 80% identical to SEQ ID NO:18, wherein the bispecific antibody derivative is administered after onset of the acute thrombotic disorder.

Yet another aspect of the present disclosure relates to a bispecific antibody derivative for use in treating an acute thrombotic disorder in a patient, comprising a first targeting domain that binds to Thrombin Activatable Fibrinolysis Inhibitor (TAFI) and comprises complementary determining regions (CDRs) represented by amino acid sequences that are at least 80% identical to each of CDR1H of SEQ ID NO:1, CDR2H of SEQ ID NO:2, CDR3H of SEQ ID NO:3, CDR1L of SEQ ID NO:4, CDR2L of SEQ ID NO:5, and CDR3L of SEQ ID NO:6; and a second targeting domain that binds to Plasminogen Activator Inhibitor-1 (PAI-1) and comprises complementary determining regions (CDRs) represented by amino acid sequences that are at least 80% identical to each of CDR1H of SEQ ID NO:7, CDR2H of SEQ ID NO:8, CDR3H of SEQ ID NO:9, CDR1L of SEQ ID NO:10, CDR2L of SEQ ID NO:11, and CDR3L of SEQ ID NO:12, wherein the bispecific antibody derivative is administered after onset of the acute thrombotic disorder and is administered without tPA. In some embodiments, the bispecific antibody derivative is administered without tPA, and within a time period that is no more than 90 minutes from the onset of the acute thrombotic disorder.

An aspect of the present invention relates to bispecific antibodies use in treating or preventing an acute thrombotic disorder in a patient. Such antibodies comprise a first targeting domain that specifically binds to Thrombin Activatable Fibrinolysis Inhibitor (TAFI) and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L; and a second targeting domain that specifically binds to Plasminogen Activator Inhibitor-1 (PAI-1) and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L.

Embodiments hereof include bispecific antibodies wherein the first targeting domain that binds to Thrombin Activatable Fibrinolysis Inhibitor (TAFI) comprises a VH region represented by an amino acid sequence that is at least 80% identical to SEQ ID NO:13 and a VL region represented by an amino acid sequence that is at least 80% identical to SEQ ID NO:14; and the second targeting domain that binds to Plasminogen Activator Inhibitor-1 (PAI-1) and comprises a VH region represented by an amino acid sequence that is at least 80% identical to SEQ ID NO:15 and a VL region represented by an amino acid sequence that is at least 80% identical to SEQ ID NO:16.

Embodiments hereof are bispecific antibodies that are humanized.

In specific embodiments these bispecific antibodies are for use in treating or preventing brain lesions resulting from an acute thrombotic disorder In specific embodiments the acute thrombotic disorder is selected from the group consisting of, acute peripheral arterial occlusion, middle cerebral artery occlusion (MCAO), and thromboembolism such as deep vein thromboembolism and lung embolism.

In certain embodiments the bispecific antibodies are for use in treating or preventing an acute thrombotic disorder in a patient in a combination treatment with tPA.

In other embodiments the bispecific antibodies are for use in treating or preventing an acute thrombotic disorder in a patient, where the treatment is performed without administration of tPA, prior, together of after the administration of the bispecific antibody.

The above mentioned acute thrombotic disorder is in specific embodiment characterized by the presence of a platelet-rich blood clot.

Another aspect of the present invention relates to methods for treating or preventing an acute thrombotic disorder in a patient, comprising the step of administering a bispecific antibody against TAFT and PAI. Herein the antibody comprises a first targeting domain that specifically binds to Thrombin Activatable Fibrinolysis Inhibitor (TAFT) and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L; and a second targeting domain that specifically binds to Plasminogen Activator Inhibitor-1 (PAI-1) and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L.

The methods of the invention provide several advantages compared to existing therapies.

The methods of the present invention wherein a diabody against TAFI and PAI-1 is used have, compared to tPA, less risks of causing intracranial haemorrhage and neurotoxicity. The diabodies of the present invention are of use in reducing lesion size in patients suffering from a brain lesion. Brain lesions may be caused by thrombotic disorders, such as stroke, acute ischemic stroke (AIS), and/or middle cerebral artery occlusion (MCAo).

Compared to tPA which has short activity upon administration (about 15 minutes), diabodies can bind to their targets for a much longer time period.

High doses of tPA can result in unwanted enzymatic activity of plasmin. The use of a high dose of diabody is less critical. Antibody which does not bind PAI-1 or TAFI has no side effects.

Compared to tPA, the diabodies show a reduction in bleeding time. Accordingly the diabodies of the present invention have the advantageous property of reducing the risk of unwanted bleeding, such as intracranial haemorrhage.

PH: variable region heavy chain anti-PAI-1 antibody; PL: variable region light chain anti-PAI-1 antibody; TH: variable region heavy chain anti-TAFI antibody; TL: variable region light chain anti-TAFI antibody; TH': humanised variable region heavy chain anti-TAFI antibody; TL': humanised variable region light chain anti-TAFI antibody.

FIG. 3A-3B shows the plasma stability and profibrinolytic effect during in vitro clot lysis. A. Graph representing stability, determined by an ELISA-based assay to measure residual binding capacity towards TAFI and PAI-1 simultaneously. (sc)Db-variants (Db-RT36A3F5x33H1F7 (Db), Db-RT36A3F5-4D5x33H1F7 (CDR-grafted Db), scDb-33H1F7xRT36A3F5 (scDb) and scDb-33H1F7xRT36A3F5-4D5 (CDR-grafted scDb)) at 10 µg/ml were incubated in citrated rat plasma at 37° C. The control Db was Db-T12D11x33H1F7] At time points zero, 1 hour and 3 hours, an aliquot was analyzed and bound protein was relatively expressed towards that of time point zero (residual binding in %, mean±SEM, n=3-9). B. Graph representing stability (% residual binding after 3 hours at 37° C. in plasma, mean±SEM, n=3-9) vs. profibrinolytic properties of (sc)Db-variants at an 8-fold molar excess over TAFI during clot lysis in rat plasma (expressed as relative lysis (mean±SEM, n=3) to that of MA-RT36A3F5 at a 4-fold molar excess over TAFI).

FIG. 4A-4B shows the profibrinolytic effect of MA (single or combined addition of MA-TCK26D6 and MA-33H1F7) and Db-TCK26D6x33H1F7 during thromboelastometric measurements using human blood (A) and blood from endotoxemic mice (B). Graph representing (A) degree of lysis (Δ L45, %; mean±SEM; n=6-12) and (B) relative Δ AUC (mean±SEM, n=3-6) in the presence of MA-33H1F7, MA-TCK26D6, the combined addition of MA or diabody. Statistical significance is indicated by asterisks (* $p<0.05$;  $p<0.01$; * $p<0.001$).

Figure 5:
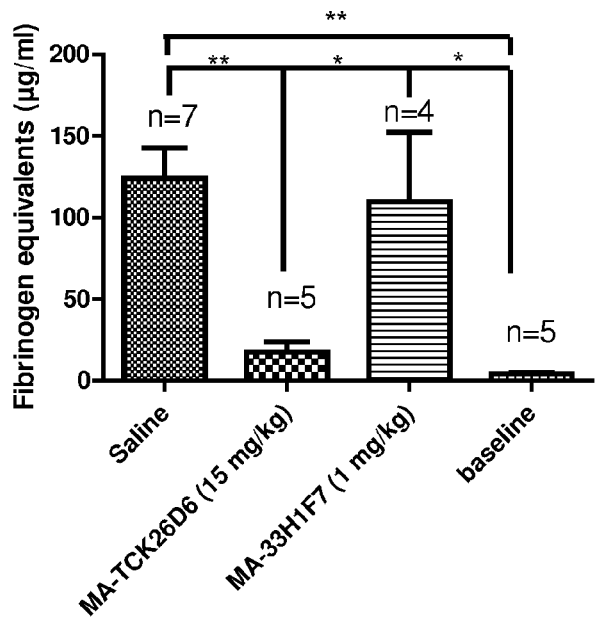

FIG. 5 shows an in vivo evaluation of MA in a thromboembolism model induced by systemic administration of thromboplastin. Graph representing fibrin contents in lungs injected with saline, MA-TCK26D6 at 5 mg/kg or MA-33H1F7 at 1 mg/kg (mean±SEM, n=5-7). Baseline levels were obtained by isolating lungs from mice without thrombotic challenge (mean±SEM, n=5). Statistical significance is indicated by asterisks (* $p<0.05$;  $p<0.01$; * $p<0.001$).

Figure 6A:
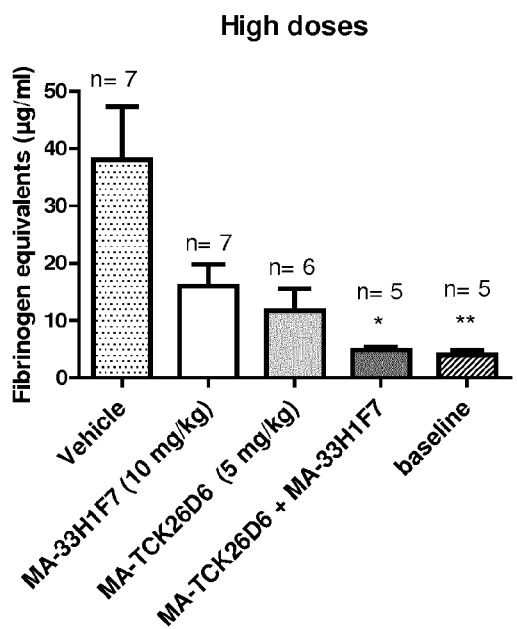
Figure 6B:
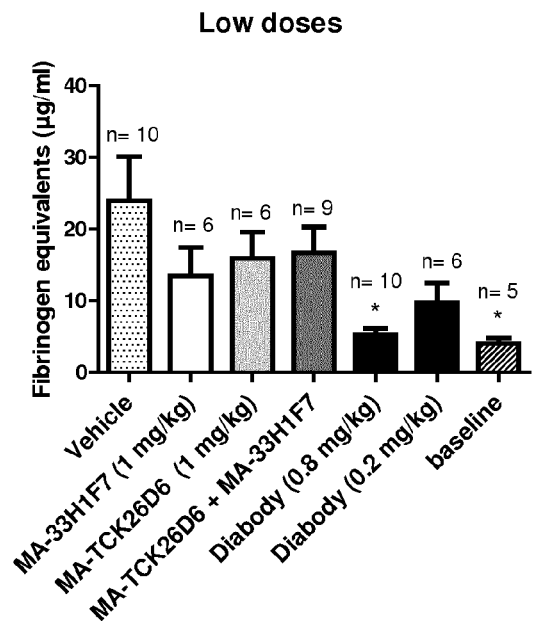

FIG. 6A-6B shows an in vivo evaluation of MA and Db in a thromboembolism model using endotoxemic mice. Graph representing fibrin contents in lungs from endotoxemic mice injected with (A.) vehicle, MA-33H1F7 at 10 mg/kg, MA-TCK26D6 at 5 mg/kg, MA-TCK26D6 at 5 mg/kg+MA-33H1F7 at 10 mg/kg or (B.) vehicle, MA-33H1F7 at 1 mg/kg, MA-TCK26D6 at 1 mg/kg, MA-TCK26D6 at 1 mg/kg+MA-33H1F7 at 1 mg/kg, Db-TCK26D6x33H1F7 at 0.8 mg/kg (mean±SEM, n=5-10). Baseline levels were obtained by isolating lungs from healthy mice without thrombotic challenge (mean±SEM, n=5). Statistical significance is indicated relative to vehicle (* $p<0.05$;  $p<0.01$; * $p<0.001$).

FIG. 7A-7G shows in vivo evaluation of MA in a mouse model of transient mechanical MCAo. FIGS. 7A and 7D show lesion size (mm$^3$), FIGS. 7B and 7E show the Bederson score (0-5), FIGS. 7C and 7F show the Grip test score (0-5), measured 24 hours post occlusion in mice treated with vehicle (PBS), negative control IgG, MA-TCK26D6 at 6 mg/kg and MA-TCK26D6 at 25 mg/kg (FIG. 7A-7C, mean±SEM, n=8-12) and vehicle (PBS), negative control IgG and MA-33H1F7 at 6 mg/kg (FIG. 7D-7F, mean±SEM, n=14-16). FIG. 7G shows fibrinogen contents in ipsilateral side of brain (fold increase vs. contralateral), measured at 24 hours post occlusion in mice treated with vehicle (PBS), negative control IgG, MA-33H1F7 at 6 mg/kg and MA-TCK26D6 at 25 mg/kg (mean±SEM, n=4-5). Statistical significance is indicated as follows: * p<0.05;  p<0.01; * p<0.001. (the control MA is MA-T30E5)

Figure 8A:
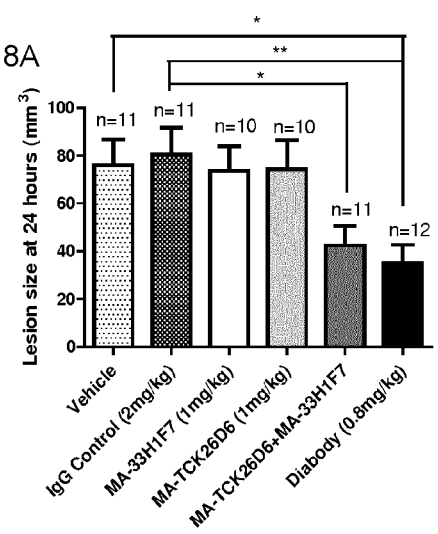
Figure 8B:
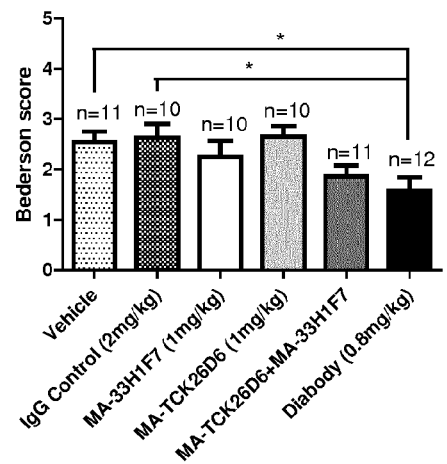
Figure 8C:
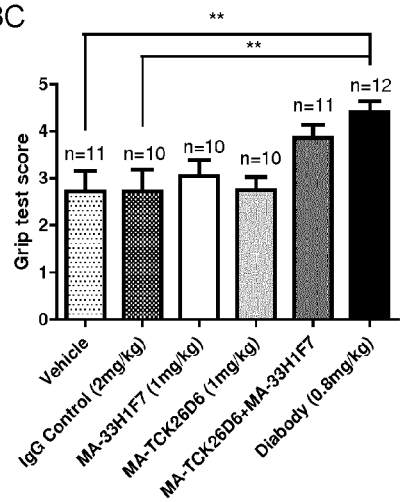
Figure 8D:
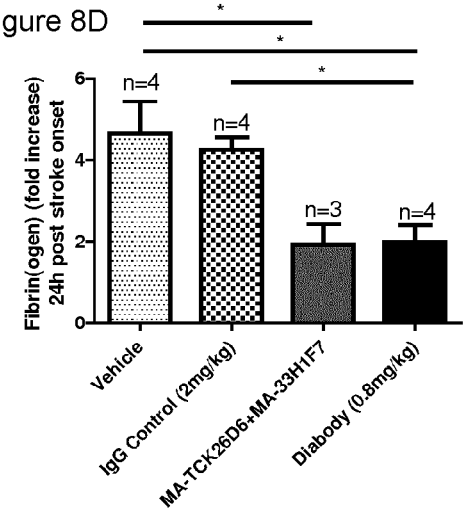

FIG. 8A-8D shows the in vivo evaluation of MA and Db in a mouse model of transient mechanical MCAo. FIG. 8A shows lesion size (mm³), FIG. 8B shows the Bederson score (0-5), FIG. 8C shows the Grip test score (0-5) measured at 24 hours post occlusion in mice treated with vehicle (PBS), negative control IgG, MA-33H1F7 at 1 mg/kg, MA-TCK26D6 at 1 mg/kg, MA-TCK26D6 at 1 mg/kg+ MA-33H1F7 at 1 mg/kg or Db at 0.8 mg/kg (mean±SEM, n=10-12). FIG. 8D shows fibrinogen contents in ipsilateral side of brain (fold increase vs. contralateral), measured at 24 hours post occlusion in mice treated with vehicle (PBS), negative control IgG, MA-TCK26D6 at 1 mg/kg+MA-33H1F7 at 1 mg/kg or Db at 0.8 mg/kg (mean±SEM, n=3-4). Statistical significance is indicated as follows: * p<0.05;  p<0.01; * p<0.001. (the control MA is MA-NB27B3)

FIG. 9A-9F shows in vivo evaluation of diabody as single treatment or as adjuvans to thrombolytic treatment in a mouse model of thrombin-induced MCAo. Graphs representing following parameters measured 24 hours post clot onset in mice treated with PBS, tPA (10 mg/kg), diabody (Db-TCK26D6x33H1F7) at 0.8 mg/kg) and combination therapy (diabody 0.8 mg/kg+tPA 10 mg/kg): (A) lesion size (mm3) (B) angiographic score (0-2) and (C) % reduction in cerebral blood flow (CBF) mean±SEM, n=6-8). Statistical significance is indicated relative to PBS (* p<0.05;  p<0.01; * p<0.001).

Additional time points after thrombin-induced occlusion are presented in FIGS. 9D, 9E, and 9F. Lesion volume (mm3) at 24 h post occlusion (upper panel) and representative T2-weighted images 24 h post occlusion (lower panel) of mice treated with vehicle, tPA (10 mg/kg), Db (0.8 mg/kg) or a combination of Db (0.8 mg/kg) and tPA (10 mg/kg) 20 min post occlusion (FIG. 9D, n=6-8), 90 min post occlusion (FIG. 9E, n=9-10) and 240 min post occlusion (FIG. 9F, n=7-9). Dotted lines delineate stroke lesions. Data are represented as mean±SEM. *, p<0.05; **, p<0.01; ns=not significant. tPA indicates recombinant tissue-type plasminogen activator; Db, diabody.

FIG. 10A-10D shows in vivo evaluation of diabody in a mouse model of $FeCl_3$-induced MCAo. Graphs representing (A) difference in cerebral blood flow (CBF) at 1 hour post occlusion (B) lesion size (mm3) (C) angiographic score (0-2) and (D) % reduction in CBF at 24 hours post occlusion, in mice treated with PBS, tPA at 10 mg/kg and diabody (Db-TCK26D6x33H1F7) at 1.6 mg/kg and at 3.6 mg/kg (mean±SEM, n=8-15). Statistical significance is indicated relative to PBS (* p<0.05;  p<0.01; * p<0.001).

FIG. 11A-11C shows In vitro and in vivo expression of scDbs against TAFI and PAI-1. Graphs comparing the following properties of a series of scDbs and their variants (A) in vitro production expressed as secreted protein in conditioned medium (B) in vitro stability in plasma at 37° C. up to 72 hours, expressed as residual binding (%) and (C) in vivo expression after intramuscular DNA injection and electroporation.

Figure 12A:
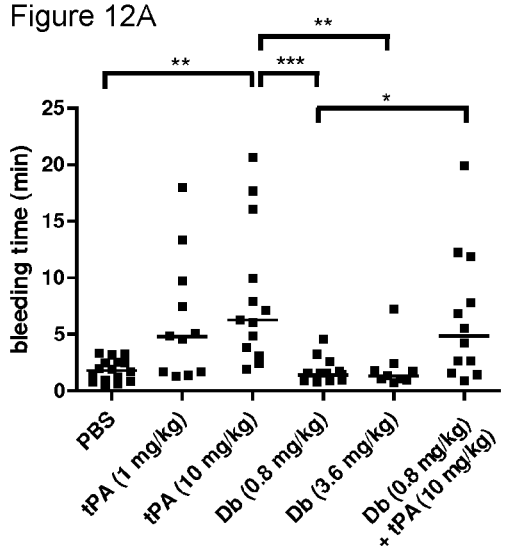
Figure 12B:
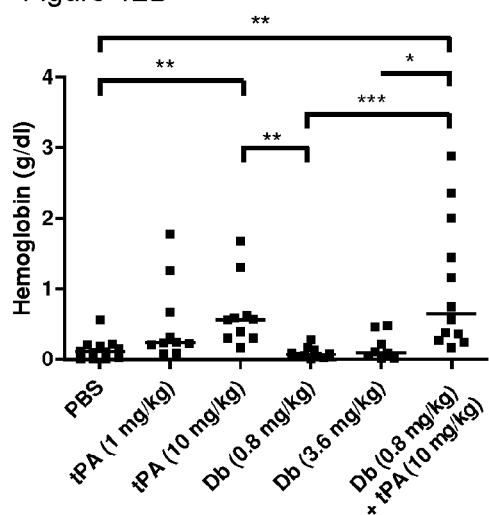

FIG. 12A-12B shows tail bleeding time and accumulative bleeding up to 60 min. in mice treated with vehicle (PBS); tPA at 1 and 10 mg/kg; diabody at 0.8 mg/kg and 3.6 mg/kg; and Db (0.8 mg/kg)+tPA (10 mg/kg). FIGS. 12A and 12B show the effect of tPA and/or diabody on bleeding time and haemoglobin levels.

Figure 13:
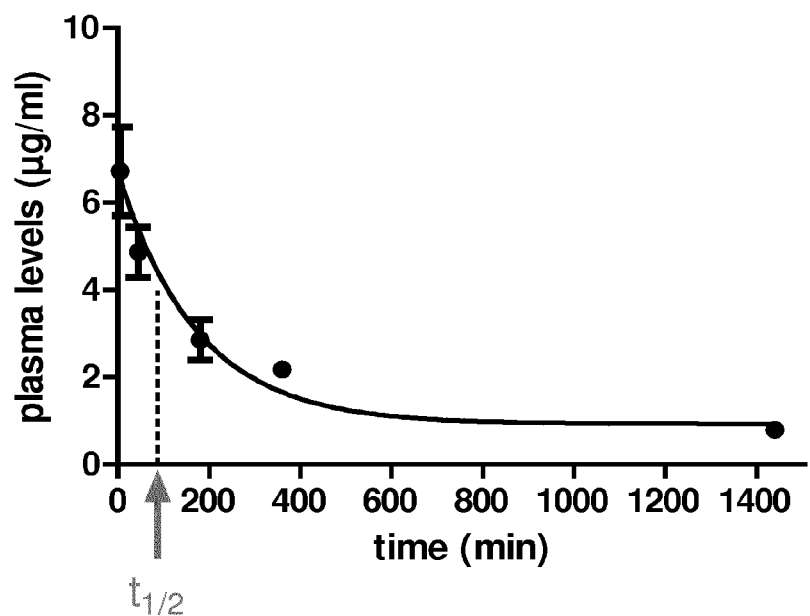

FIG. 13 shows systemic pharmacokinetics of the diabody after intravenous injection. Graph shows plasma levels (µg/ml, mean±SEM) plotted against time (min) after IV injection of diabody at 0.8 mg/kg in 6 mice (red arrow indicates circulating half-life=121 min). FIG. 13A shows the time (in minutes) until initial cessation of tail bleeding as monitored in mice, and (B) accumulative bleeding (haemoglobin loss) up to 60 min, measured as haemoglobin (g/dL) (median, n=9-16 mice/group; *, p<0.05;  p<0.01; * p<0.005). tPA indicates recombinant tissue-type plasminogen activator; Db, diabody.

Figure 14A:
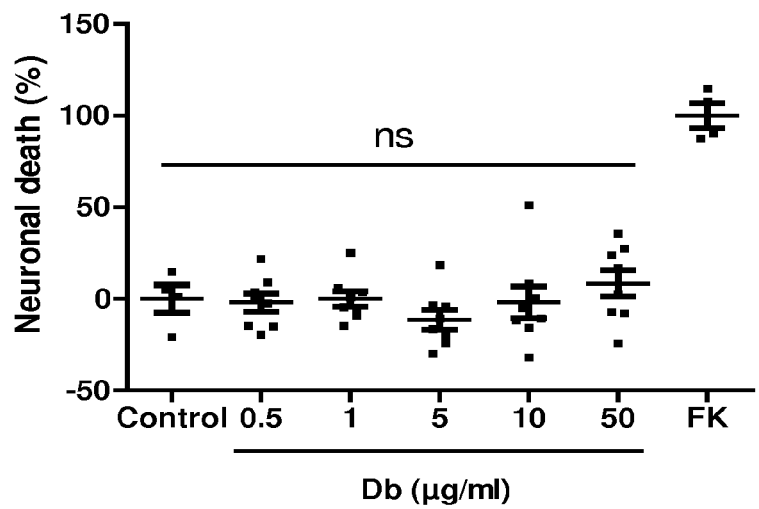
Figure 14B:
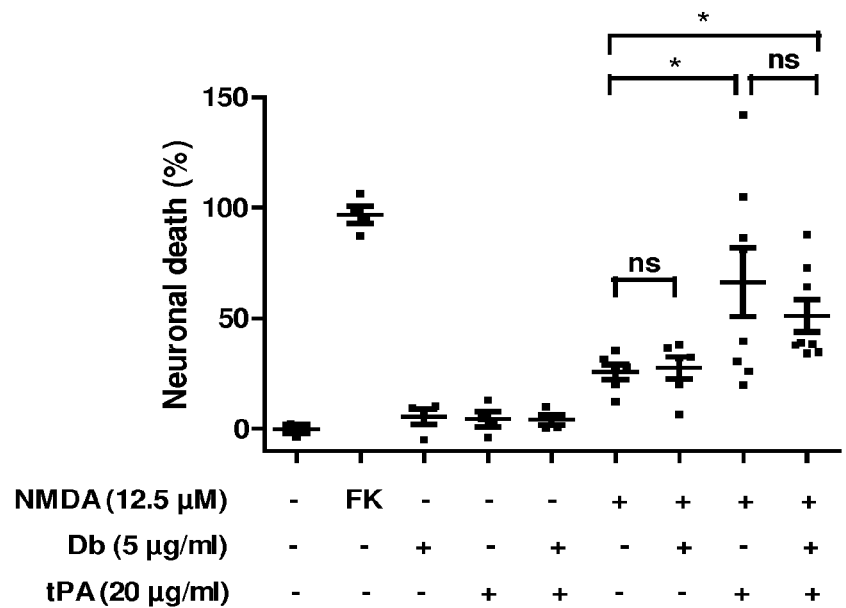

FIG. 14A-14B shows the evaluation of the effect of the diabody (Db) on cortical neuronal death with or without NMDA-induced excitotoxicity. In FIG. 14A, cortical neurons were exposed to NMDA (as a full kill condition (FK); 500 µmol/L) or diabody (0.5-50 µg/ml); In FIG. 14B cortical neurons were exposed to NMDA (500 µmol/L (full kill, FK) or 12.5 µmol/L), Db (5 µg/ml) or rtPA (20 µg/ml), either alone or in combination, during 24 hours before measurement of neuronal death (N=2 independent cultures, n=2-4, *p<0.05; ns=not significant). tPA indicates recombinant tissue-type plasminogen activator; Db, diabody; NMDA, N-methyl-D-aspartate.

DETAILED DESCRIPTION

The present disclosure relates to the use of bispecific antibody derivatives in treating thrombotic disorders. The bispecific antibody derivatives target TAFI and PAI-1 and inhibit both proteins in a dual targeting strategy. In some embodiments, the bispecific antibody derivative is a diabody known as Db-TCK26D6x33H1F7, and may be used in treating acute thrombotic disorders. In some embodiments, the bispecific antibody derivative is administered after onset of the acute thrombotic disorder. In certain embodiments, the bispecific antibody derivative is administered to patients at risk for developing thrombotic disorders, either acute or chronic thrombotic disorders.

Exemplary sequences of bispecific antibody derivatives or portions thereof are described herein (SEQ ID NOS: 1-18). In addition, bispecific antibody derivatives of the present disclosure may be identical, substantially identical, homologous, or similar to the exemplary sequences described herein.

"Sequence identity" refers to two amino acid sequences or subsequences that are identical, or that have a specified percentage of amino acid residues that are the same (e.g., 60% or 65% identity, preferably, 70%-95% identity, more preferably, >95% identity), when compared and aligned for maximum correspondence over a window of comparison, or over a designated region, as measured using a sequence comparison algorithm as known in the art, or by manual alignment and visual inspection. In certain embodiments, the described identity exists over a region that is at least about 5 to 10 amino acids in length.

Specific "designated regions" in the context of the present invention are the CDR regions or the present invention. These CDR regions are typically conserved (100% sequence identity compared to the reference sequence), although one or more substations may be allowable in one or more CDRs as long as the functional properties of the reference antibody are maintained. With CDR regions ranging from 5 to almost 20 amino acids, typical embodiments of a modified CDR of an antibody sequences have a sequence identity in the CDR region which is at least 75, 80, 85, 90, 92, 94, 95% to the reference CDR sequence.

Outside the CDR regions the sequence of a variable heavy or light chain may be less restricted while still maintaining the function of the antibody. Thus a variable chain may be at least 75, 80, 85, 90, 92, 95, 97, 98 or 99% identical to a reference sequence of a variable chain while one, two, or all three CDR sequences have one amino acid difference with the corresponding reference CDR sequence or wherein all CDR regions are identical with those of the reference sequence.

A difference at a certain position can be a change into any of the other 19 amino acids or can be a so-called "conservative substitution"

It is a well-established principle of protein chemistry that such "conservative amino acid substitutions," can frequently be made in a protein without altering either the conformation or the function of the protein. Such changes include substituting any of isoleucine (I), valine (V), and leucine (L) for any other of these hydrophobic amino acids; aspartic acid (D) for glutamic acid (E) and vice versa; glutamine (Q) for asparagine (N) and vice versa; and serine (S) for threonine (T) and vice versa. Substituting any of tryptophan (W), tyrosine (Y), and phenylalanine (F) for any other of these aromatic amino acids and vice versa. Other substitutions can also be considered conservative, depending on the environment of the particular amino acid and its role in the three-dimensional structure of the protein. For example, glycine (G) and alanine (A) can frequently be interchangeable, as can alanine and valine (V). Methionine (M), which is relatively hydrophobic, can frequently be interchanged with leucine and isoleucine, and sometimes with valine. Lysine (K) and arginine (R) are frequently interchangeable in locations in which the significant feature of the amino acid residue is its charge and the differing pK's of these two amino acid residues are not significant. "Bispecific antibody" refers to an antibody based construct that can simultaneously bind to two different antigens. In the context of the present invention this means specific binding to TAFI and specific binding to PAI-1.

"Diabody" refers to a specific type of bispecific antibody which comprise a heavy chain variable domain (VH) of one antibody connected to a light-chain variable domain (VL) of another antibody on the same polypeptide chain (VH-VL). By using a linker that is too short to allow pairing between the two domains on the same chain, the domains are forced to pair with the complementary domains of another chain and create two antigen-binding sites. In a diabody antigen-binding sites point in opposite directions.

Typically these are complexes of ScFv constructs. Different configurations are possible. A possible configuration is a complex of two polypeptides, namely:

a fusion protein of the VH region of an anti-TAFI antibody and the VL region of an anti PIA-1 antibody, with a fusion protein of the VL region of an anti-TAFI antibody and the VH region of an anti-PIA-1 antibody. Other examples are a single peptide chain with two VH and two VL regions, yielding tandem scFv's. Or scFv's with linker peptides that are too short for the two variable regions to fold together (about five amino acids), forcing scFvs to dimerize.

"Targeting domain" refers to the part of the bispecific antibody that is required to obtain specific antigen binding (antigen binding domain) with one of the antigens.

"Fibrinolysis" refers to the degradation of fibrin within a blood clot.

"Thrombolysis" refers to the degradation of a blood clot by inter alia, breakdown of fibrin threads and other structural elements which form a clot.

TAFI (Thrombin-Activatable Fibrinolysis Inhibitor) is also known as Carboxypeptidase B2 (CPB2), Carboxypeptidase U (CPU) or plasma carboxypeptidase B (pCPB). TAFI is an enzyme that reduces fibrinolysis by removing fibrin C-terminal residues that are important for the binding and activation of plasminogen.

PAI-1 (Plasminogen Activator Inhibitor-1 (PAI-1), is also known as endothelial plasminogen activator inhibitor or serpin E1. PAI- is a serine protease inhibitor that tissue plasminogen activator (tPA) and urokinase (uPA).

Thrombus refers to a clot in the cardiovascular system formed during life from blood constituents. Clots may be occlusive or attached are attached to vessel or heart wall without obstructions. Exemplary types of thrombi are fibrin clots formed by deposits of fibrin and white or pale clots mainly composed of platelets.

"tPA" (tissue plasminogen activator) refers to the wild type protein, but also covers modified versions known as reteplase, tenecteplase "Thrombosis" is a condition characterized by the formation of a blood clot inside a blood vessel, and is thought to result from an abnormality in one or more of hypercoagulability, endothelial injury/dysfunction, and hemodynamic changes of stasis and turbulence (together known as Virchow's triad). Thrombosis can lead to vessel blockage at the site of clot formation, or to vessel blockage at a distance from the site of origin (i.e., embolism). In both cases, obstruction of the vessel disrupts the supply of oxygen to the tissues supplied by the vessel, resulting in hypoxia, anoxia, and infarction. Accordingly, many pathological conditions arise from thrombosis, ranging from deep vein thrombosis to pulmonary embolism to arterial thrombosis which cause heart attacks and strokes, and more.

"Thrombotic disorders" as used herein includes but is not limited to deep vein thrombosis (DVT), pulmonary embolism (PE), coronary artery disease (CAD) and acute coronary syndrome (AC S), central retinal artery occlusion (CRAO), age related macular degeneration (AMD) and thrombotic neurological disorders, including stroke, acute ischemic stroke (AIS), middle cerebral artery occlusion (MCAo), acute peripheral arterial occlusion (APAO) and more.

The disorders may also be thrombotic neurological disorders comprising diseases, disorders or conditions which directly or indirectly affects the normal functioning or anatomy of a subject's nervous system, including but not limited to, cerebrovascular insufficiency, cerebral ischemia or cerebral infarction such as stroke, retinal ischemia (diabetic or otherwise), glaucoma, retinal degeneration, multiple sclerosis, ischemic optic neuropathy, reperfusion following acute cerebral ischemia, perinatal hypoxic-ischemic injury, or intracranial haemorrhage of any type (including, but not limited to, epidural, subdural, subarachnoid or intracerebral haemorrhage).

In certain embodiments, the thrombotic disorder is hereditary in origin. In certain embodiments, the thrombotic disorder is acquired. The thrombotic disorder may be acute, chronic and/or recurring. In certain embodiments, the thrombotic disorder is acute, and is at least one of acute ischemic stroke (AIS), middle cerebral artery occlusion (MCAo), thromboembolism, deep vein thrombosis, myocardial infarction (MI), pulmonary embolism, peripheral arterial disease, thrombosis of liver and/or kidneys, or catheter blockage. The thrombotic disorder may be an occlusive syndrome in the cerebral vascular system, for example, causing cerebral infarcts due to stroke or ischemic stroke. In some embodiments, the acute thrombotic disorder is AIS. In certain embodiments, the acute thrombotic disorder is MCAo.

Bispecific Antibody Derivatives for Use in Treating Thrombotic Disorders

Bispecific antibody derivatives represent the smallest format currently available to achieve bispecificity when starting from two IgG's to allow efficient penetration into the blood clot. The dual specificity confers inhibition of TAFI and PAI-1 at the same time, same localization, and same concentration, which leads to a similar pharmacokinetic profile and biodistribution. In some embodiments, the bispecific antibody derivatives for use in treating thrombotic disorders are based on monoclonal antibodies (MAs). For example, exemplary MAs which target TAFI are MA-RT36A3F5 and MA-TCK26D6 [6, 7] [Hillmayer et al. cited above; Vercauteren (2011) cited above], while exemplary MAs which targets PAI-1 are MA-33H1F7 and MA-MP2D2 [De Brock cited above, Van De Craen cited above]. One exemplary bispecific antibody derivative is DbTCK26D6x33H1F7 [Wyseure T et al. (2013) *J Thromb Haemost.* 11, 2069-2071]. In certain embodiments, the efficacy of bispecific antibody derivatives surpasses that of either MA administered alone.

In some embodiments, the bispecific antibody derivative comprises a first targeting domain that binds to Thrombin Activatable Fibrinolysis Inhibitor (TAFI) and comprises complementary determining regions (CDRs) represented by amino acid sequences that are at least 80% identical to each of CDR1H of SEQ ID NO:1, CDR2H of SEQ ID NO:2, CDR3H of SEQ ID NO:3, CDR1L of SEQ ID NO:4, CDR2L of SEQ ID NO:5, and CDR3L of SEQ ID NO:6; and a second targeting domain that binds to Plasminogen Activator Inhibitor-1 (PAI-1) and comprises complementary determining regions (CDRs) represented by amino acid sequences that are at least 80% identical to each of CDR1H of SEQ ID NO:7, CDR2H of SEQ ID NO:8, CDR3H of SEQ ID NO:9, CDR1L of SEQ ID NO:10, CDR2L of SEQ ID NO:11, and CDR3L of SEQ ID NO:12.

For example, the bispecific antibody derivative may comprise a first targeting domain that binds to Thrombin Activatable Fibrinolysis Inhibitor (TAFI) and comprises a VH region represented by an amino acid sequence that is at least 80% identical to SEQ ID NO:13 and a VL region represented by amino acid sequence that is at least 80% identical to each of SEQ ID NO:14; and a second targeting domain that binds to Plasminogen Activator Inhibitor-1 (PAI-1) and comprises a VH region represented by an amino acid sequence that is at least 80% identical to SEQ ID NO:15 and a VL region represented by amino acid sequence that is at least 80% identical to SEQ ID NO:16.

In certain embodiments, a bispecific antibody derivative comprises a first domain that comprises an amino acid sequence that is at least 80% identical to SEQ ID NO:17; and a second domain that comprises an amino acid sequence that is at least 80% identical to SEQ ID NO:18.

SEQ ID NO:17 comprises at the N terminal side the sequence with SEQ ID NO:13 and at the C terminal side the sequence of SEQ ID NO 16.

SEQ ID NO:18 comprises at the N terminal side the sequence with SEQ ID NO:15 and at the C terminal side the sequence of SEQ ID NO 14.

In some embodiments, the amino acid sequences in the bispecific antibody derivatives are at least 80%, 85%, 90%, 95%, 99% or 100% identical to the amino acid sequences disclosed in SEQ ID NO:1-18. For example, in SEQ ID NO:2, the second amino residue (marked "X") may be either Val or Ile (and correspondingly, in SEQ ID NO:13, the fifty first amino acid residue (marked "X") may be either Val or Ile. In certain embodiments, the amino acid sequences in the bispecific antibody derivatives have variations in amino acid residues which do not significantly affect the binding properties of the bispecific antibody derivatives to their targets.

In some embodiments, variations in amino acid residues may affect the stability of the bispecific antibody derivative.

In some embodiments, the bispecific antibody derivative, for example, as disclosed herein is humanized.

The bispecific antibodies disclosed herein may not be neurotoxic in contrast to tPA, and may be used for reducing lesion size in patients suffering from a brain lesion. Brain lesions may be caused by thrombotic disorders, such as stroke, acute ischemic stroke (AIS), and/or middle cerebral artery occlusion (MCAo). Thrombo-inflammation in patients suffering from a thrombotic disorder may be reduced by the bispecific antibodies.

A dangerous side effect of thrombolytic treatment is increased bleeding risk, for example from intracranial haemorrhage. The bispecific antibodies described herein may be used to reduce or minimize the bleeding and/or bleeding risk, as they did not prolong bleeding in an animal model for bleeding risk, in contrast to tPA. In addition, the relatively short half-life of the bispecific antibodies may minimize side effects such as intracranial haemorrhage in patients treated with the bispecific antibodies.

A further consequence of thrombotic disorders such as stroke, acute ischemic stroke (AIS), and/or middle cerebral artery occlusion (MCAo) are neurological impairments. In some embodiments, the bispecific antibodies disclosed herein may be used for treating neurological impairments, such as motor, sensory, and/or cognitive impairments. Impairments and/or limitations in limb flexion, lateral push, grip, and more may be treated with the bispecific antibodies disclosed herein.

Administration

Timing of thrombolytic treatment is critical. In the case of acute thrombotic disorders such as acute myocardial infarction, acute ischemic stroke, or acute massive pulmonary embolism, tPA is typically administered to break down clots within 15 hours of the stroke, for example, as soon as possible after onset of stroke symptoms, at 0-6 hours, or at 4.5 hours. Similarly, in some embodiments, the bispecific antibody derivative as disclosed herein is administered between 0-15 hours after onset of symptoms of the thrombotic disorder. The thrombotic disorder may be an acute thrombotic disorder, such as a stroke, for example, AIS or MCAo. In certain embodiments, the bispecific antibody is administered at 0.5 hours, 1 hour, 1.5 hours, 3 hours, 4 hours, 4.5 hours, or more hours after onset of symptoms of the thrombotic disorder, for example, at 4.5 hours after onset of symptoms. In some embodiments, the bispecific antibody derivative is administered 12 hours after onset of symptoms of the thrombotic disorder. The bispecific antibody derivative may be administered intravenously, or directly into the blood clot.

To date, plasminogen activators such as tPA are the only thrombolytic agents approved by the US FDA, and plasminogen activators such as tPA remain the primary first-line treatment for acute thrombotic disorders. However, some patients do not respond to tPA treatment and further interventions are needed. Accordingly, in some embodiments, the bispecific antibody derivative is administered together with a plasminogen activator, for example, tPA. For example, the bispecific antibody derivative may be administered simultaneously with tPA, as a combination treatment. The bispecific antibody derivative may also be administered after tPA is administered first. In some embodiments, the bispecific antibody derivative is administered 1 hour after administration of tPA. If a patient does not respond to tPA within 1 hour, the bispecific antibody derivative may be administered as a further intervention.

A surprising and unexpected result of the present disclosure is that bispecific antibody derivatives were equally effective in the presence or in the absence of tPA when administered up to 90 minutes post-occlusion. Additionally, bispecific antibody derivatives had a superior thrombolytic effect than tPA. Thus, the bispecific antibody derivatives disclosed herein may be used as thrombolytic agents in place of a plasminogen activator such as tPA. One aspect of the present disclosure relates to the use of the bispecific antibody derivatives disclosed herein for use in treating an acute thrombotic disorder, wherein the bispecific antibody derivative is administered without tPA. In certain embodiments, the acute thrombotic disorder is characterized by the presence of a fibrin-rich blood clot. In some embodiments, the acute thrombotic disorder is characterized by the presence of a platelet-rich blood clot. In some embodiments, the bispecific antibody derivative is administered without tPA during a time period of up to 90 minutes after the onset of the acute thrombotic disorder, for example, 0-90 minutes after onset. Thus, the bispecific antibody derivative may be administered at 0, 10, 15, 20, 30, 40, 45, 50, 60, 70, 80, or 90 minutes after onset of the acute thrombotic disorder.

In some embodiments, when treatment for an acute thrombotic disorder is administered at least 90 minutes of onset of the acute thrombotic disorder, the bispecific antibody derivative is administered together with tPA. The combination of bispecific antibody derivative and tPA may be administered at 90 minutes after onset, or at 2 hours, 2.5 hours, 3 hours, 3.5 hours, 4 hours, 4.5 hours, 5 hours, 5.5 hours, 6 hours, or more after onset. In certain embodiments, administration of the diabody does not lead to deleterious neurotoxic effects. When administered in combination with tPA, the bispecific antibody derivative may potentiate the thrombolytic effect of tPA without potentiating the adverse side effects observed with tPA alone. The bispecific antibody derivatives as disclosed herein may also be combined with antiplatelet treatments such as aspirin, clopidogrel, and dipyridamole; anticoagulant treatments such as heparin, warfarin, and dabigatran; and/or surgical interventions such as revascularization, carotid endartectomy, carotid angioplasty, intra-arterial thrombolysis, and mechanical embolus removal in cerebral ischemia (MERCI).

The diabodies of the present invention can be delivered as one bolus or can be administered over a longer period of time.

The total amount of diabody, administered to a patient can range from 0.1, 0.5, 1 or kg body weight up to 2 or 5 mg/kg body weight.

Since the administration of an excess of antibody has no detrimental side effects, a total dosis of 10, 20, 40, 80 or 100 mg of diabody may be administered regardless from the body weight of the patient.

Prevention

Thrombotic disorders are common, particularly in elderly populations and/or in patients who have been previously affected by a thrombotic disorder. Thrombotic disorders may be either acute or chronic. Additional risk factors for stroke such as AIS and/or MCAo include advanced age, alcohol use, atherosclerosis, atrial fibrillation, use of birth control pills, diabetes, poor diet, family history of stroke, fibromuscular dysplasia, high blood pressure, high cholesterol, hypercoagulability (either hereditary or acquired), inflammation, low birth weight, migraine, obesity, patent foramen ovale, physical inactivity, postmenopausal hormone therapy, previous stroke, certain races/ethnicities, sickle cell disease, sleep apnoea, transient ischemic attack, tobacco use, and more. Risk factors for venous thrombosis, such as deep vein thrombosis (DVT) which is a frequent cause of pulmonary embolism, include but are not limited to advanced age, major surgery, orthopaedic surgery, cancer, immobilization, pregnancy, antiphospholipid syndrome, trauma, minor leg injury, previous venous thrombosis, use of oral contraceptives, hormonal replacement therapy, central venous catheters, inflammatory diseases or autoimmune disease, nephrotic syndrome, obesity, infection, HIV, polycythaemia vera, and chemotherapy, as well as hereditary risk factors including but not limited to antithrombin deficiency, protein C deficiency, protein S deficiency, Factor V Leiden, Prothrombin G20210A, dysfibrogenemia, and non-O blood type. Additional risk factors include but are not limited to low levels of protein S, activated protein C resistance, high Factor VIII levels, hyperhomocysteinemia, and/or high levels of fibrinogen, Factor IX, and/or Factor XI.

A further aspect of the present disclosure relates to a bispecific antibody for use in patients at risk for developing an acute or chronic thrombotic disorder, comprising a first targeting domain that binds to Thrombin-Activatable Fibrinolysis Inhibitor (TAFI) and comprises complementary determining regions (CDRs) represented by amino acid sequences that are at least 80% identical to each of CDR1H of SEQ ID NO:1, CDR2H of SEQ ID NO:2, CDR3H of SEQ ID NO:3, CDR1L of SEQ ID NO:4, CDR2L of SEQ ID NO:5, and CDR3L of SEQ ID NO:6; and a second targeting domain that binds to Plasminogen Activator Inhibitor-1 (PAI-1) and comprises complementary determining regions (CDRs) represented by amino acid sequences that are at least 80% identical to each of CDR1H of SEQ ID NO:7, CDR2H of SEQ ID NO:8, CDR3H of SEQ ID NO:9, CDR1L of SEQ ID NO:10, CDR2L of SEQ ID NO:11, and CDR3L of SEQ ID NO:12, wherein the bispecific antibody derivative is administered before onset of the acute or chronic thrombotic disorder. In certain embodiments, the acute or chronic thrombotic disorder is thromboembolism.

For example, the bispecific antibody derivative may comprise a first targeting domain that binds to Thrombin-Activatable Fibrinolysis Inhibitor (TAFI) and comprises a VH region represented by an amino acid sequence that is at least 80% identical to SEQ ID NO:13 and a VL region represented by an amino acid sequence that is at least 80% identical to SEQ ID NO:14; and a second targeting domain that binds to Plasminogen Activator Inhibitor-1 (PAI-1) and comprises a VH region represented by an amino acid sequence that is at least 80% identical to SEQ ID NO:15 and a VL region represented by an amino acid sequence that is at least 80% identical to SEQ ID NO:16.

In certain embodiments, a bispecific antibody derivative comprises a first domain that comprises an amino acid sequence that is at least 80% identical to SEQ ID NO:17; and a second domain that comprises an amino acid sequence that is at least 80% identical to SEQ ID NO:18.

In some embodiments, the amino acid sequences in the bispecific antibody derivatives are at least 80%, 85%, 90%, 95%, 99% or 100% identical to the amino acid sequences disclosed in SEQ ID NO:1-18. For example, in SEQ ID NO:2, the second amino residue (marked "X") may be either Val or Ile (and correspondingly, in SEQ ID NO:13, the fifty first amino acid residue (marked "X") may be either Val or Ile.

Incorporation By Reference

All publications and patents mentioned herein are hereby incorporated by reference in their entirety as if each individual publication or patent was specifically and individually indicated to be incorporated by reference. In case of conflict, the present application, including any definitions herein, will control.

Equivalents

While specific embodiments of the subject invention have been discussed, the above specification is illustrative and not restrictive. Many variations of the invention will become apparent to those skilled in the art upon review of this specification and the claims below. The full scope of the invention should be determined by reference to the claims, along with their full scope of equivalents, and the specification, along with such variations.

EXAMPLES

Having provided a general disclosure, the following examples help to illustrate the general disclosure. These specific examples are included merely to illustrate certain aspects and embodiments of the disclosure, and they are not intended to be limiting in any respect. Certain general principles described in the examples, however, may be generally applicable to other aspects or embodiments of the disclosure.

Example 1

Figure 1A:
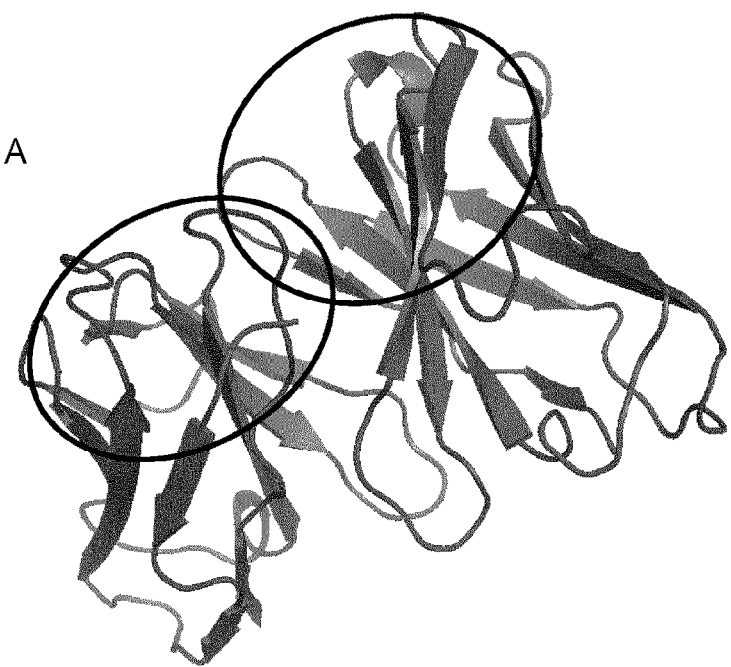
FIG. 1A-1B shows the expression levels of CDR-grafted scFv. A. Modeled structure of CDR of MA-RT36A3F5 (circles) in the framework of scFv-4D5. B. Immunoblot showing periplasmic extracts containing CDR-grafted scFv-RT36A3F5-4D5 (lane 1), scFv-T12D11 as control (lane 2), scFv-RT36A3F5-T12D11 (lane 3) and scFv-RT36A3F5-4D5DM (lane 4), detected via anti-His-tag polyclonal antibody.
Figure 1B:
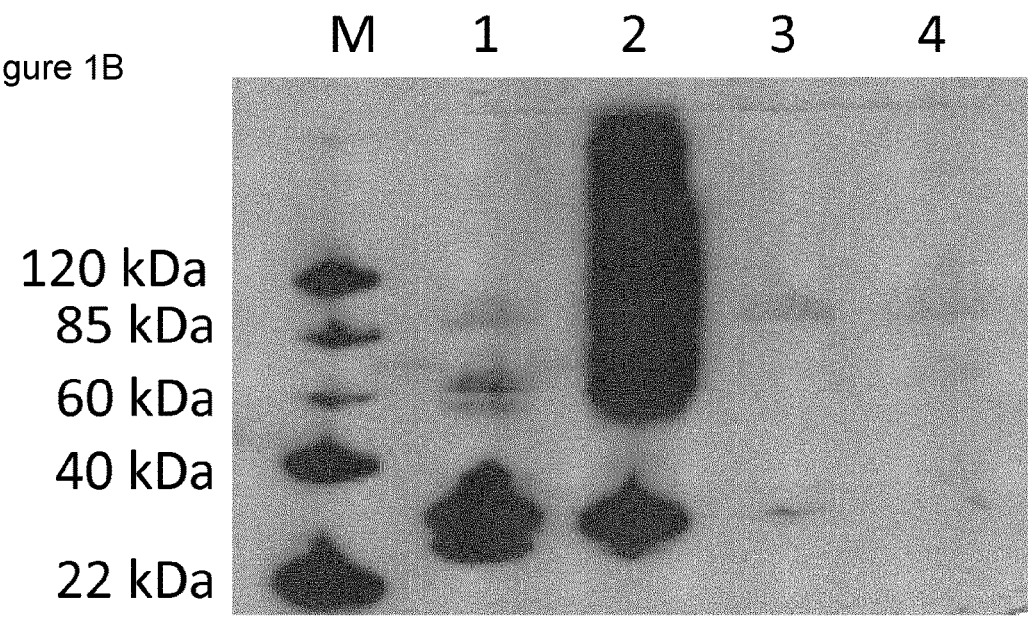

Improving Expression and Efficacy of an Unstable Bispecific Inhibitor (Db-RT36A3F5x33H1F7) Against TAFI and PAI-1 Through Antibody Engineering A. CDR-Grafting to Engineer Stable Variable Domains In a previous study, scFv-RT36A3F5 was generated, but could not be produced by bacteria and corresponding Db-RT36A3F5x33H1F7 was found to be unstable resulting in a diminished effect on clot lysis. Thus, the variable domains of MA-RT36A3F5 were optimized by complementarity determining region (CDR)-grafting onto the stable scaffolds of scFv-4D5 (FIG. 1A) [Jung S. & Plückthun A. (1997) *Protein Eng.* 10, 959-966. This article discloses the 4D5 humanised antibody used in the CDR grafting]. Two approaches were performed: (i) structure alignment-based strategy of scFv-RT36A3F5 and of scFv-4D5, generating scFv-RT36A3F5-4D5DM (in collaboration with prof. Marc Demaeyer) and (ii) evidence-based strategy, generating scFv-RT36A3F5-4D5 [Ewert S. et al. (2004) *Methods.* 34, 184-199]. The latter approach was also performed on the stable scaffolds of scFv-T12D11 (an anti_TAFI antibody disclosed in de Develter et al. 2008 *J Thromb Haemost.* 6, 1884-1889, generating scFv-RT36A3F5-T12D11. Western blot analysis revealed that solely scFv-RT36A3F5-4D5 was properly expressed and secreted (FIG. 1B, lane 1) and therefore, these CDR-grafted variable domains were used in corresponding (sc)Db constructs.

B. Production of Bispecific Antibody-Based Inhibitors from MA-RT36A3F5 and MA-33H1F7

Figure 2:
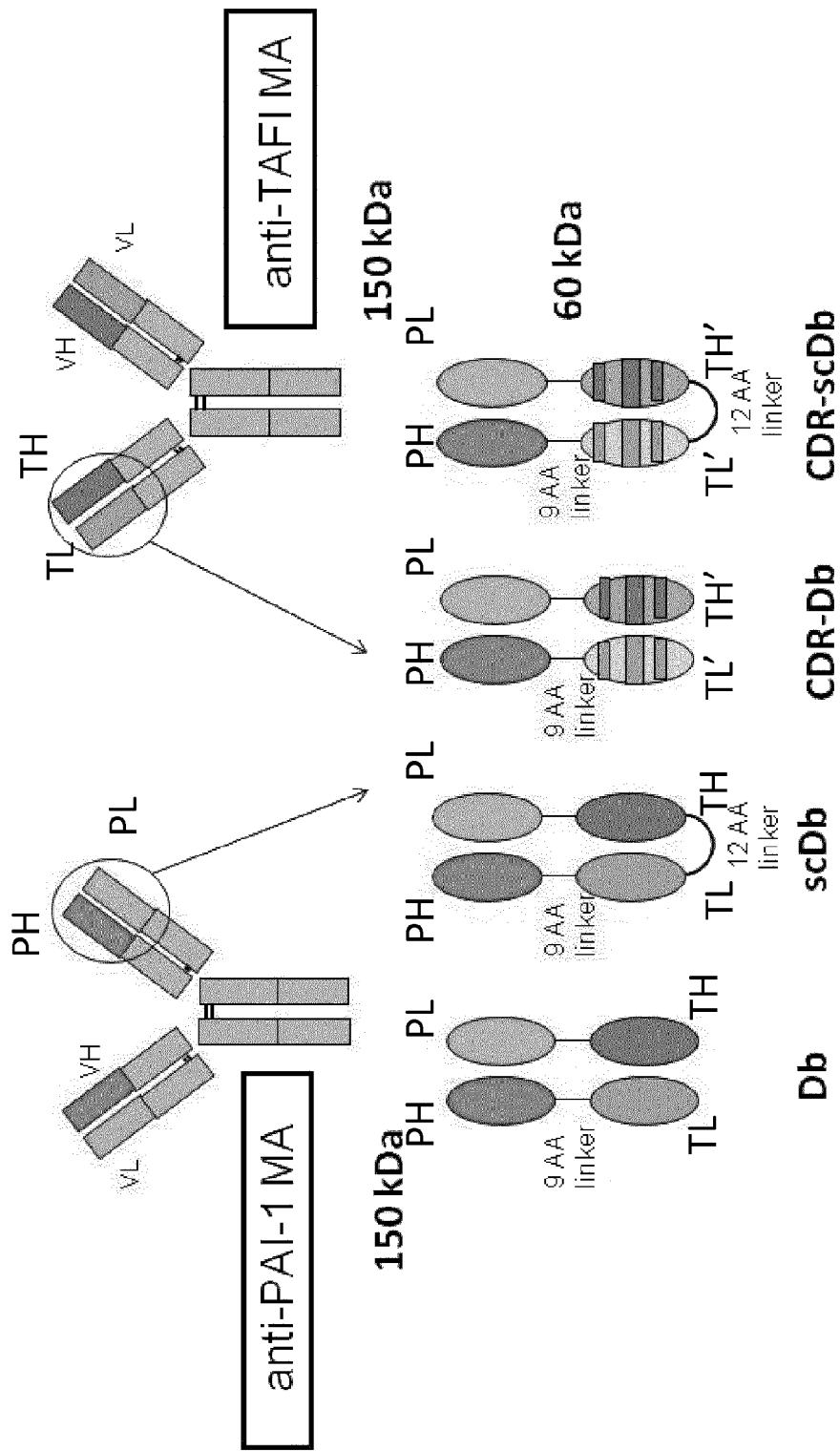
FIG. 2 shows a schematic representation of bispecific inhibitors: Db-RT36A3F5x33H1F7 (Db), Db-RT36A3F5-4D5x33H1F7 (CDR-grafted Db), scDb-33H1F7xRT36A3F5 (scDb) and scDb-33H1F7xRT36A3F5-4D5 (CDR-grafted scDb).

Four bispecific inhibitors were formed out of MA-RT36A3F5 and MA-33H1F7: Db-RT36A3F5x33H1F7 (Db), Db-RT36A3F5-4D5x33H1F7 (CDR-grafted Db), scDb-33H1F7xRT36A3F5 (scDb with an additional flexible linker between the variable domains of MA-RT36A3F5) and scDb-33H1F7xRT36A3F5-4D5 (CDR-grafted scDb) (FIG. 2). As a result of CDR-grafting, bacterial and eukaryotic expression of Db and scDb, respectively, were elevated (for CDR-grafted Db approximately 1.5 mg/L culture corresponding to a two-fold increase vs. Db and for CDR-grafted scDb 11±1 mg/L culture medium corresponding to a ten-fold increase vs. scDb).

C. Inhibitory Properties of Bispecific Inhibitors

Inhibitory properties of the parental antibodies were preserved in Db, CDR-grafted Db and CDR-grafted scDb as confirmed by functional assays. Inhibitory properties of scDb could not be evaluated due to insufficient production.

D. Stability and Profibrinolytic Properties of Diabodies in Citrated Rat Plasma

Out of all constructs, only CDR-grafted scDb exhibited a similar stability as the control diabody, Db-T12D11x33H1F7 (88±13% residual binding activity after three hours at 37° C.; FIG. 3A). With a relative profibrinolytic effect of 0.81±0.23, CDR-grafted scDb was also the most potent construct compared to MA-RT36A3F5 (FIG. 3B). The contribution of the effect of the PAI-1 inhibiting moiety could not be evaluated in the plasma-based assay system due to the low baseline plasma levels of PAI-1.

In conclusion, our efforts to increase the plasma stability of an unstable bispecific antibody-based inhibitor against rat TAFI and PAI-1 resulted in a CDR-grafted scDb, exhibiting a seven-fold increased stability and profibrinolytic effect. This antibody derivative cross-reacts with mouse TAFI and mouse PAI-1, allowing further in vivo evaluation in mice and rats.

Example 2

In Vitro Evaluation of the Profibrinolytic Properties of a Novel Bispecific Inhibitor Against TAFI and PAI-1

A. Generation of Db-TCK26D6x33H1F7

Based on the successful generation of stable scFvs with preserved inhibitory capacity of the respective parental antibodies (MA-TCK26D6 and MA-33H1F7), Db-TCK26D6x33H1F7 was generated. This diabody contains two polypeptide chains as depicted in FIG. 2 left bottom. The first one is a fusion protein of the VH chain of the anti TAFI antibody and the VL chain of the anti PAI-1 antibody. The second one is a fusion protein of the VL chain of the anti TAFI antibody and the VH chain of the anti PAI-1 antibody.

The production level of Db-TCK26D6x33H1F7 was approximately 2 mg/L culture.

B. Characterization of the Inhibitory Effect Towards TAFI and PAI-1

Inhibitory properties of the parental antibodies against human and mouse TAFI and PAI-1 were preserved in Db-TCK26D6x33H1F7 as confirmed by functional assays. Moreover, Db-TCK26D6x33H1F7 remained stable after incubation in human, mouse and rat plasma after 8 hours at 37° C.

C. Effect of Db-TCK26D6x33H1F7 During Thromboelastometric Analysis in Whole Blood To evaluate the profibrinolytic effect due to TAFI and PAI-1 inhibition, Db-TCK26D6x33H1F7 was incubated in human whole blood from four individuals and its effect was analysed by thromboelastometry [Wyseure T. et al. (2013) *J. Thromb. Haemost.* 11, 2069-2071]. The combined addition of both MAs as well as the addition of diabody facilitated fibrinolysis to a very significant degree (p<0.001), whereas the addition of a single MA caused only a modest effect (FIG. 4A).

The effect of Db-TCK26D6x33H1F7 was also evaluated in whole blood from mice. Since PAI-1 levels are extremely low in mice (serum levels, mean±SD, n=4, 3.0±0.3 ng/ml for mice vs. 267±114 ng/ml for humans), thromboelastometric analysis in blood from mice is insensitive to PAI-1. To increase PAI-1 levels in mouse blood, we induced experimental endotoxemia through intraperitoneal injection of LPS (0.5 mg/kg) prior to collection of blood for thromboelastometric analysis. The combined addition of both MAs as well as the addition of diabody facilitated fibrinolysis to a significant degree (p<0.05), whereas the addition of a single MA caused no significant effect (FIG. 4B).

Thus, Db-TCK26D6x33H1F7 exhibits strong profibrinolytic properties in vitro.

Example 3

In Vivo Evaluation of the Profibrinolytic Properties of a Bispecific Inhibitor Against TAFI and PAI-1

1. Complementary Effect of Dual TAFI/PAI-1 Inhibition after Systemic Thrombotic Challenge Mice, pre-treated with a dose of MA-TCK26D6 or MA-33H1F7 targeting all circulating antigen, were subjected to thromboembolism by systemic administration of thromboplastin. Fibrin deposition in lungs was only decreased to baseline levels upon administration of a TAFI inhibitor (FIG. 5). Since PAI-1 levels are extremely low in mice, no effect of PAI-1 inhibition was detected.

To evaluate simultaneous inhibition of TAFI and PAI-1 in this model, endotoxemia was induced to upregulate PAI-1 levels in plasma. Fibrin deposition in the lungs was reduced through TAFI inhibition with MA-TCK26D6 (5 mg/kg) or through PAI-1 inhibition with MA-33H1F7 (10 mg/kg). However, this reduction did not reach a maximal degree. After administering a mixture of MA-TCK26D6 (5 mg/kg) and MA-33H1F7 (10 mg/kg), fibrin levels in lungs returned to baseline (FIG. 6A). This maximal effect disappeared when lowering the dosages of MA to 1 mg/kg (FIG. 6B). Upon treatment with diabody (Db-TCK26D6x33H1F7 at 0.8 mg/kg, i.e. a dose which targets the same amount of TAFI and PAI-1 as achieved with the combined MA each at 1 mg/kg), a maximal effect of fibrin clearance from lungs was obtained.

As demonstrated, simultaneous inhibition of TAFI and PAI-1 results in an additive effect on fibrin removal in a thromboembolism model which is most effective through Db-TCK26D6x33H1F7.

2. Effect of Db-TCK26D6x33H1F7 in Mouse Models for Acute Ischemic Stroke
i. Monofilament-mediated MCAo Transient occlusion was accomplished by advancing a monofilament into the MCA. This model was used to assess the effect of TAFI and/or PAI-1 inhibition on cerebral ischemia/reperfusion injury. This model typically yields large lesion volumes in untreated mice which have measurable neurological/motor defects. Paramount in preclinical evaluation of stroke is to assess neurological parameters in addition to lesion size. Interestingly, in this model, tPA has a well-described deleterious effect through aggravating neuronal damage after focal cerebral ischemia [Wang Y F et al. (1998) Nat Med. 4, 228-231]. Treatment with either MA-TCK26D6 at 25 mg/kg or MA-33H1F7 at 6 mg/kg caused reduced brain lesions (FIG. 7A, 7D) and concomitant neurological and motor recovery 24 hours post occlusion (FIG. 7B-C, 7E-F). In addition, the brains of treated mice contained less fibrin(ogen) in the ipsilateral side compared to those of control mice (FIG. 7G). The control IgG in control IgG was MA-T30E5 in FIG. 7 and MA-NB27B3 in FIG. 8. Treatment with either one of the parental antibody at 1 mg/kg did not alter lesion sizes or neurological/motor scores 24 hours post occlusion (FIG. 8A-C). However, the combined administration of the antibodies substantially reduced brain lesions 1.9-fold (FIG. 8A). Moreover, the diabody at a corresponding dose caused a similar reduction in lesion size (2.3-fold) however concomitantly improved neurological and motor scores (FIG. 8A-C). Lesion sizes were 76±11 mm$^3$ with vehicle, 81±11 mm$^3$ with control IgG, 43±8 mm$^3$ with combination of MA and 35±8 mm$^3$ with diabody. In addition, western blot analysis revealed that the combination of parental antibodies or diabody effectively reduced massive fibrin deposition induced by reperfusion injury by at least 2-fold (FIG. 8D; p<0.05; n=3-4 mice/group).

ii. Thrombin-mediated MCAo

A model of thromboembolic stroke by thrombin injection was used in which clots are rich in fibrin and thus susceptible to be thrombolysed by tPA. The efficacy of the diabody was compared to that of tPA, the current thrombolytic agent. In order to mimic the clinical procedure of thrombolysis, the administration of tPA was performed by an initial bolus of 10% volume followed by 90% infusion during 40 min because of the short half-life of circulating tPA (~5 min) [Chandler W L et al. (1997) Circulation. 96, 761-768]. 24 h post occlusion, complete recanalization of the arterial lumen occurred in all groups including the vehicle group (median angiographic score=2, FIG. 9B). At the same time point, Speckle contrast imaging showed a 40% reduction in tissue perfusion in the MCA territory distal to the occlusion in the vehicle group (FIG. 9C). Interestingly, brain perfusion was virtually restored by the combination of diabody and tPA (FIG. 9C; p<0.05 vs. vehicle; n=6-8 mice/group), while diabody or tPA separately did not significantly increase perfusion. Lesion volume was reduced by administration of tPA, however this reduction was not statistically significant (37±13 mm$^3$ vs. 26±12 mm$^3$; FIG. 9A; p=0.203; n=6-8 mice/group). In contrast, early diabody administration (0.8 mg/kg) at 20 minutes post-occlusion, regardless of the co-administration of tPA, substantially reduced lesion volume at 24 h (15±4 mm$^3$ for diabody and 15±8 mm$^3$ for diabody+tPA; p<0.01 and p<0.05 vs. vehicle respectively; n=6-8 mice/group FIG. 9A). [FIGS. 9A and 9D show the same conditions]. Treatments were also delayed to a clinically more relevant time point, e.g. 90 min post occlusion (intermediate time point) [Hacke W. et al. (2004) Lancet 363, 768-774], complete recanalization was also observed at 24 h post occlusion in all treatment groups (median angiographic score=2). Intermediately delayed administration of diabody nor infusion of tPA had any beneficial effect on the lesion volume (25±3 mm$^3$ (vehicle) vs. 24±3 mm$^3$ (tPA) vs. 21±4 mm$^3$ (Db); FIG. 9E; n=9-10 mice/group). However, at the same treatment time point diabody administration prior to tPA infusion resulted in a significantly reduced lesion volume (15±2 mm$^3$ (Db+tPA); p<0.05 vs. vehicle; n=10 mice/group; FIG. 9E).

None of the treatments had an effect on lesion sizes in this model when administered at 240 min post occlusion (late time point, FIG. 9F).

At 90 min post stroke onset and onwards, tPA treatment does not always result in a beneficial outcome, presumably because of the increased stability of the clot (i.e. clot retraction) resulting in thrombolytic resistance, the neurotoxic effect of tPA to the progressively damaged brain and/or the increased risk for haemorrhagic transformation. In the present example, neither tPA treatment nor diabody treatment at 90 min post occlusion reduced the lesion volumes.

However, the combined treatment of the diabody and tPA resulted in a significantly decreased lesion volume, underscoring the potential clinical benefit of adding the diabody to current thrombolytic treatment. At a later treatment time point of 4 h post occlusion, a tendency towards increased lesion volumes after tPA treatment, alone or with diabody, was observed (FIG. 9F). In correspondence to the in vitro neurotoxicity data (FIG. 14), the diabody also had no deleterious effect in vivo.

iii. FeCl$_3$-mediated MCAo

Figure 10A:
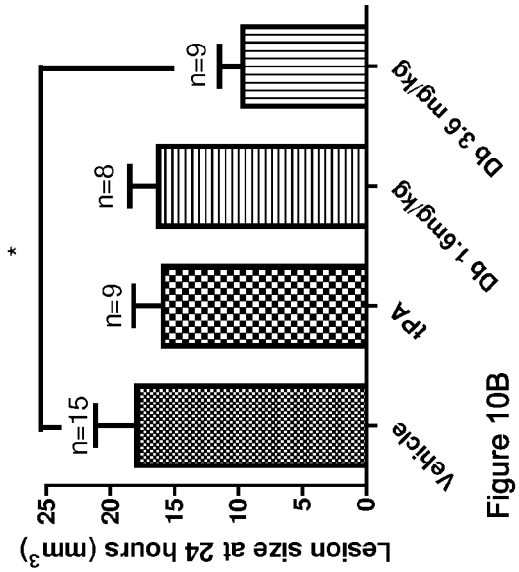
Figure 10B:
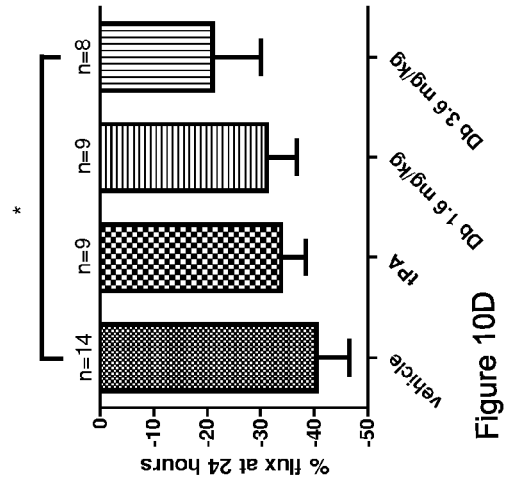
Figure 10C:
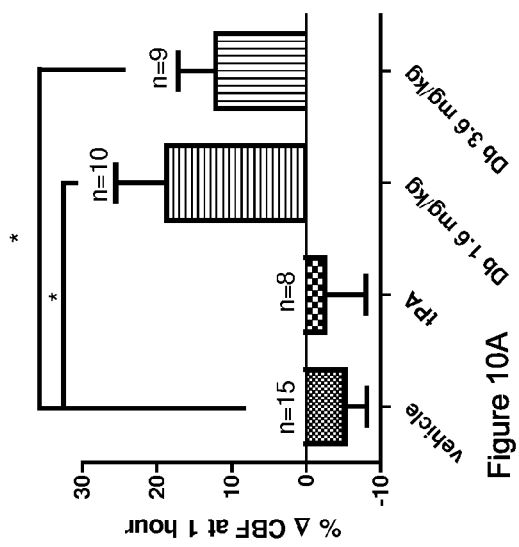
Figure 10D:
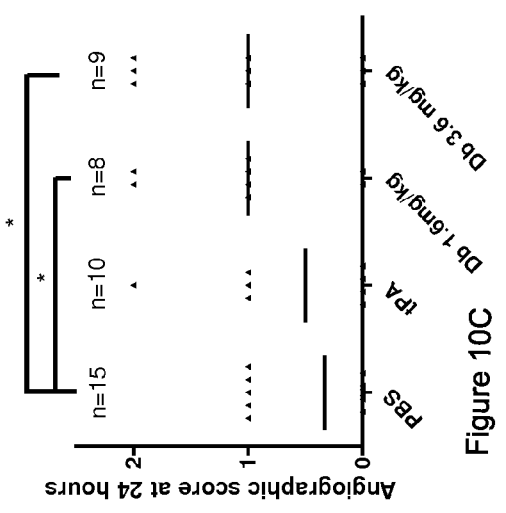

Platelet-rich clots are more resistant to treatment with tPA [Kim E Y et al. (2006) Neurology 67, 1846-1848]. Therefore, a FeCl$_3$-induced MCAo model was used in which clots are rich in platelets and thus mimic this clinically relevant issue. As expected, tPA was not effective in (i) increasing CBF 1 h post occlusion (laser Doppler tracings; FIG. 10A), (ii) ameliorating the angiographic score 24 h post occlusion (FIG. 10C), (iii) reducing lesion volume 24 h post occlusion (FIG. 10C) or (iv) increasing brain reperfusion 24 h post occlusion (Speckle contrast imaging, FIG. 10D). The diabody administered at 1.6 mg/kg significantly increased CBF 1 h (FIG. 10A; $p<0.05$ vs. vehicle; n=8-15 mice/group) and the angiographic score 24 h post occlusion (FIG. 10C; $p<0.05$ vs. vehicle; n=8-15 mice/group), however no amelioration of brain perfusion or lesion volume was observed 24 h post occlusion (FIG. 10B, D). In contrast, at 3.6 mg/kg the diabody significantly increased CBF at 1 h post occlusion (FIG. 10A; $p<0.05$ vs. vehicle; n=8-15 mice/group) which resulted in a significantly increased angiographic score (FIG. 10C; $p<0.05$; n=8-15 mice/group), reduced lesion volume (FIG. 10B; $p<0.05$ vs. vehicle; n=8-15 mice/group), and increased brain perfusion (FIG. 10D; $p<0.05$ vs. vehicle; n=8-14 mice/group) at 24 h.

In conclusion, the strong fibrinolytic enhancer designated as Db-TCK26D6x33H1F7 showed a robust in vivo performance in a set of mouse models of stroke.

Example 4

In Vivo Expression of Bispecific Inhibitors Against TAFI and PAI-1 scDbs were expressed in vivo as they can be efficiently produced in eukaryotic cells. The following constructs were generated against TAFI and PAI-1 and cloned into pcDNA3.1: scDb-33H1F7xRT36A3F5, scDb-TCK26D6x33H1F7 and scDb-TCK26D6xMP2D2. In vitro expression levels in HEK293T cells ranged from 0.6-1.1 µg/ml (FIG. 11A). scDb-33H1F7xRT36A3F5 was further optimized by CDR-grafting into scDb-33H1F7xRT36A3F5-4D5. which resulted in a ten-fold higher expression and seven-fold increased plasma stability (after three hours of incubation at 37° C.). In mice, peak plasma levels after gene transfer were 584±79 ng/ml (n=6) and 188±19 ng/ml (n=4) for scDb-33H1F7xRT36A3F5-4D5 at day 3 and scDb-TCK26D6x33H1F7 at day 6, respectively, however no expression of scDb-TCK26D6xMP2D2 could be detected (FIG. 11C). As the obtained plasma levels were too low for pharmacological evaluation, pharmacokinetics of the scDbs were altered to prolong the circulating half-life. To this end, an affinity-engineered albumin binding domain [Jonsson A et al. (2008) Protein Eng Des Sel. 21, 515-527] was fused to the C-terminus of scDb-TCK26D6x33H1F7 and scDb-TCK26D6xMP2D2, which were the only constructs that remained stable during incubation in plasma at 37° C. up to three days (FIG. 11B). The albumin binding constructs were designated as scDb-TCK26D6x33H1F7xABDH and scDb-TCK26D6xMP2D2xABDH. Unfortunately, a two- to four-fold reduction in expression was observed in vitro for these constructs (FIG. 11A). However, in vivo expression levels were two-fold increased at day 9 (287±28 ng/ml, n=5) for the albumin binding variant of scDb-TCK26D6x33H1F7, whereas expression of the albumin binding variant of scDb-TCK26D6xMP2D2 was not detectable (FIG. 11C).

Example 6

Assessment of Bleeding and Pharmacokinetics

Additional tail bleeding experiments were performed to compare the effects of an IV injection of tPA at two different doses: the dose equivalent to that used in clinical practice for humans (1 mg/kg) and to that typically used in mice (10 mg/kg). Diabody (Db-TCK26D6x33H1F7) was injected at 0.8 mg/kg and 3.6 mg/kg. IV administration of diabody up to 3.6 mg/kg did not alter tail bleeding time or accumulative haemoglobin loss after 60 min tail incubation, whereas both doses of tPA prolonged bleeding time and increased haemoglobin loss (FIG. 12A and FIG. 12B; n=9-16 mice/group). Co-administration of diabody (0.8 mg/kg) and tPA (10 mg/kg), the treatment regimen tested in the thrombin-mediated MCAo model, did not further increase the tail bleeding time nor haemoglobin loss compared to tPA administration alone.

Alternatively, no cerebral haemorrhages were observed in either mechanical or thrombotic MCAo stroke models after any treatment.

The circulating half-life of diabody after IV administration in mice was 121 min (FIG. 13) which allows bolus injection as acute treatment.

Materials & Methods

Production of Diabodies (Db) and Single-chain Diabodies (scDb)

Antibody derivatives were produced by cloning the variable domains (VH, VL) from a hybridoma cell line producing monoclonal antibody. DNA fragments containing Db or scDb were designed for bacterial production (via periplasmic secretion) and eukaryotic production (via extracellular secretion), respectively. The DNA fragments were synthetically produced and were further cloned into pSKID2 for production of Db in E. coli RV308 and into pcDNA3.1. for production of scDb using HEK293T cells. The His6-tagged antibody derivatives were purified on a Ni$^{++}$-column and prior to in vivo evaluation endotoxins were removed by anion-exchange chromatography.

Quantification of (sc)Db (sc)Dbs were quantified by an ELISA based on the simultaneous binding towards PAI-1 and TAFI. Briefly, a microtiter plate coated with mouse PAI-1 was used to bind (sc)Db and detection was performed via subsequent incubation with mouse TAFI, followed by addition of MA-TCK32G12-HRP against TAFI, which was subsequently developed using o-phenylenediamine as chromogenic substrate.

TAFI Neutralization Assay

The ability of antibody derivatives to inhibit TAFI was quantified by using a chromogenic assay to measure residual TAFIa activity and was compared to the inhibitory properties of the parental monoclonal antibody (MA). TAFI was incubated with MA or sc(Db), at concentrations ranging from 0.06- to 8-fold molar ratio over TAFI, before or after activation by thrombin/thrombomodulin or plasmin, depending on the working mechanism of the MA. Residual TAFIa activity was determined using Hippuryl-Arg as a substrate, followed by a colorimetric reaction.

PAI-1 Neutralization Assay

The ability of antibody derivatives to inhibit active PAI-1 was quantified by using a plasminogen-coupled chromogenic method and was compared to the inhibitory properties of the parental MA. PAI-1 was pre-incubated (2 hours, room temperature) with MA or (sc)Db at concentrations ranging from 0.06- to 32-fold molar ratio over PAI-1. After a consecutive incubation with tPA (15' 37° C.), plasminogen was added and the extent of conversion to plasmin, was quantified by a chromogenic substrate.

In Vitro Plasma Clot Lysis Assay

Pooled rat citrated plasma was pre-incubated (10', 37° C.) with MA or sc(Db), followed by the addition of $CaCl_2$ and t-PA. Clot lysis was then monitored over time through measurement of the turbidity ($OD_{405\ nm}$) by a microtiter plate reader. The degree of fibrinolysis was expressed as the area under the curve over a time frame of 180 min. The retrieved data were normalized to the value obtained in the presence of MA (at a concentration corresponding to the equivalent number of binding sites to the respective antigens as that of sc(Db)).

Rotational Thromboelastometry

Citrated whole blood from four healthy donors or from mice (healthy or endotoxemic by intraperitoneal injection of LPS (0.5 mg/kg) six hours prior to the start of the experiment) was pre-incubated with MA or Db (at concentrations yielding an equivalent number of binding sites to the respective antigens). Clotting and subsequent fibrinolysis was initiated by thromboplastin, $CaCl_2$ and tPA. For human blood, fibrinolysis was determined by the decrease in amplitude at 45 minutes after initial clotting relative to the maximal amplitude (L (%)=[$(A_{max}-A_{45})/A_{max}$]*100). In each run, baseline lysis ($L_{wo}$) was determined using the same blood sample without MA or Db ($L_{wo}$ never exceeded 12%). Specific inhibitor-enhanced lysis was then determined as $\Delta L$ (%)=$L_{inhibitor}-L_{wo}$. For mouse blood, specific inhibitor-enhanced fibrinolysis was determined as the difference in area under the curve (AUC from clotting time to clotting time+120 minutes) between saline ($AUC_{wo}$) and treated condition ($AUC_{inhibitor}$) relative to the $AUC_{wo}$ (relative $\Delta$ AUC=[($AUC_{wo}-AUC_{inhibitor})/AUC_{wo}$]*100.

In Vivo Models

Thromboembolism Model

MA, diabody or saline (0.9% NaCl) was injected intravenously (IV) in overnight fasted non-anesthetized SWISS mice (healthy or endotoxemic by intraperitoneal injection of LPS (0.5 mg/kg) three hours prior to the start of the experiment). Five minutes later, thromboembolism was induced by IV injection of thromboplastin. Mice were anaesthetized by pentobarbital (60 mg/kg intraperitoneally) and 15 minutes post thrombotic challenge lungs were perfused with 10 IU/ml heparin. Then the lungs were isolated and homogenized. Washed homogenate of (left) lung was incubated with 2 µM microplasmin in order to convert fibrin into solubilized fibrin degradation products for subsequent quantification of fibrin degradation products using a cross-reacting ELISA towards mouse fibrinogen. Fibrin content in lungs was expressed as fibrinogen equivalents (µg/ml).

Thrombin- and $FeCl_3$-mediated MCAo Model

Anesthetized SWISS mice (by inhalation of 2% isoflurane/oxygen mixture) were placed on a stereotaxic device to expose the right middle cerebral artery (MCA) by craniectomy. In situ occlusion, as confirmed by Laser Doppler flowmetry, was performed by micro-injection of murine alpha-thrombin into the MCA [Orset C et al. (2007) Stroke. 38, 2771-2778] or by application of a filter paper saturated with 20% $FeCl_3$ [Karatas H et al. (2011) *J Cereb Blood Flow Metab*. 231, 1452-1460]. Db or PBS (vehicle) was injected IV 15 minutes post clot onset. Five minutes later, tPA (10 mg/kg) or saline was administered via a tail vein catheter (10% as bolus and 90% infused over 40 minutes). 24 hours after initial occlusion, cerebral blood flow was mapped on the ipsi- and contralateral side by exposing the skull to a Speckle contrast imager (Moor FLPI-2, Moor instruments). Reduction of blood flow was expressed relative to the contralateral side. Brain lesion volume was determined by T2-weighted MRI, angiographic score in the MCA (0=occlusion, 1=partial recanalization and 2=complete recanalization) was determined by MR angiography and T2*-weighted MRI was used to exclude the occurrence of haemorrhages.

To assess different treatment time points in the thrombin-mediated model, diabody (Db) or vehicle (PBS) was injected IV via a tail vein catheter at certain time points post occlusion: an early (15 min), intermediate (90 min) or late (240 min) time point. Five min after diabody or vehicle administration, tPA (10 mg/kg) or saline was administered IV (10% as bolus and 90% infused over 40 min). Brain lesion volume was determined by T2-weighted MRI and angiographic score in the MCA (0=occlusion, 1=partial recanalization and 2=complete recanalization) was determined by MR angiography and T2*-weighted MRI was used to exclude the occurrence of haemorrhages.

Monofilament-mediated MCAo Model

After a midline skin incision in the neck of anesthetized C57BL/6 mice (by inhalation of 2% isoflurane/oxygen mixture), the proximal common carotid artery and the external carotid artery were ligated. The origin of the right MCA was occluded by inserting a standardized silicon rubber-coated 6.0 nylon monofilament via the right internal carotid artery. After 60 minutes of in situ occlusion, the intraluminal monofilament was withdrawn and 5 minutes after reperfusion, MA or PBS was injected IV. 24 hours after initial occlusion, mice were subjected to functional tests: the modified Bederson test and the grip test to assess neurological and motoric function, respectively. Mice were then euthanized and brains were harvested to determine lesion volumes (by 2,3,5-triphenyl-tetrazolium chloride staining).

Neurological Tests 24 hours post occlusion (MCAo model), mice were subjected to the modified Bederson test and the grip test to assess global neurological function and motoric function, respectively. This modified Bederson test uses the following scoring system: 0, no deficit; 1, forelimb flexion; 2, decreased resistance to lateral push; 3, unidirectional circling; 4, longitudinal spinning; 5, no movement.

The grip test was performed in which a mouse was placed on a wooden bar (3 mm diameter, 40 cm long) attached to 2 vertical supports 40 cm above a flat surface. When placing the mouse on the bar midway between the supports, the experiment was rated according to the following system: 0, falls off; 1, hangs onto bar by 2 forepaws; 2, same as for 1, but attempts to climb onto bar; 3, hangs onto bar by 2 forepaws plus 1 or both hind paws; 4, hangs onto bar by all 4 paws plus tail wrapped around bar; 5, escape (mouse able to reach one of the supports). Assessment was performed blinded.

Lesion Quantification 24 hours post occlusion (MCAo model), mice were euthanized. Brains were quickly harvested and cut into 2-mm-thick coronal sections using a mouse brain slice matrix. The presence of cerebral haemorrhages was assessed visually.

The slices were stained with 2% 2,3,5-triphenyl-tetrazolium chloride (Sigma-Aldrich, St. Louis, Mo.) in PBS to distinguish healthy tissue from unstained infarctions. Stained slices were photographed with a digital Nikon D70 camera, and infarct areas (white) were measured blindly using Image J software (National Institutes of Health, Bethesda, Md.).

Protein Extraction and Western Blot Analysis

Ischemic tissue including the cortex and basal ganglia was dissected from formalin-fixed TTC-stained brain slices and homogenized in RIPA buffer (25 mmol/L Tris pH 7.4, 150 mmol/L NaCl, 1% NP40) containing 0.1% SDS and 0.25% protease inhibitor cocktail (Roche) as previously described with slight modifications. 39 Samples were homogenized using a CLI12 mixer followed by incubation at 4° C. for 20 min and subsequent sonication on ice. Then tissue lysates were centrifuged at 15,000×g for 20 min at 4° C. and supernatants were subjected to Western blot analysis as follows. 30 µg of total protein was loaded, electrophoresed on a SDS-polyacrylamide gel and transferred to a nitrocellulose membrane. After blocking for 1 h with blocking buffer (5% nonfat dry milk, 50 mmol/L Tris-HCl pH 7.5, 150 mmol/L NaCl, 0.05% Tween-20) membranes were incubated with either anti-Fibrinogen polyclonal antibody (AP00766PU-N, Acris; diluted 1:500) or anti-Actin MA (MAB1501, Millipore; diluted 1:500) at 4° C. overnight or for 1 hour, respectively. Then membranes were washed followed by incubation with HRP-conjugated goat anti-rabbit IgG (Jackson ImmunoResearch; diluted 1:14000) (fibrinogen) or goat anti-mouse IgG (Dako; diluted 1:2000) (actin) for 60 min at room temperature. Blots were developed using SuperSignal West Pico Chemiluminescent Substrate (Thermo Scientific) and signal was detected with the LAS-4000 mini imager (GE Healthcare).

Tail Bleeding Assay

Mouse tail vein bleeding times were determined with a tail-clipping assay, as described previously. Mice were administered with PBS, diabody, tPA as a single administration or diabody 5 min prior to tPA as a co-administration via proximal tail vein injection. Five min post injection, a distal 3 mm segment of the tail was clipped and the amputated tail was immersed immediately in 0.9% isotonic saline at 37° C. Bleeding time was monitored until initial cessation of bleeding (i.e. no rebleeding within 30 s). Experiments were conducted blinded to treatments. Accumulative haemoglobin loss was determined over a period of 60 min after tail-clipping. Subsequent to centrifugation (10 min at 2000×g), blood cells were resuspended in 1 mL isotonic saline, and the haemoglobin content was measured on a Cell-Dyn 3500R counter (Abbott, Diegem, Belgium).

Determination of Circulating Half-life

Db-TCK26D6x33H1F7 (0.8 mg/kg) was administered IV via tail vein injection in mice (n=6). Prior to the experiment, blood was withdrawn on 0.38% trisodium citrate (=presample). Post injection, blood was withdrawn on 0.38% trisodium citrate at several time points: 5 min, 45 min, 3 hours, 6 hours and 24 hours. Diabody concentrations in corresponding plasma samples were determined by an ELISA based on the simultaneous binding of the diabody towards PAI-1 and TAFI. Wells of polystyrene microtiter plates were incubated with 200 µl recombinant mouse PAI-1 in PBS (pH 7.4; 4 µg/ml) for 72 hours at 4° C., emptied and treated for two hours with PBS supplemented with 1% (m/v) bovine serum albumin. After washing, serial two-fold dilutions (180 µl) of plasma samples were added to the wells and incubated overnight at 4° C. Then, the wells were washed and incubated with 170 µl mouse TAFI (0.1 µg/ml) for 2 hours at room temperature. Subsequently, plates were washed and 160 µl HRP-conjugated MA-TCK32G12 (directed against TAFI) was added to the wells followed by incubation for 2 hours at room temperature. All washing steps were performed with PBS containing Tween 80 (0.002%) and dilutions were made in PBS containing Tween 80 (0.002%) and bovine serum albumin (0.1% m/v). The ELISA was developed using 150 µl of 0.1 mol/L citrate-0.2 mol/L sodium phosphate buffer, pH 5.0, containing 300 µg/mL o-phenylenediamine and 0.01% hydrogen peroxide. After 30 min at room temperature the peroxidase reaction was stopped with 50 µl 4 mol/L $H_2SO_4$. The absorbance was measured at 492 nm. Db-TCK26D6x33H1F7 was used as calibrator.

Gene Transfer by In Vivo Electroporation

Anesthetized SWISS mice (by inhalation of 2% isoflurane/oxygen mixture) were pre-bled. Both quadriceps muscles received an injection of hyaluronidase three hours prior to injection of plasmid DNA (pcDNA3.1. containing scDb), followed by electroporation. Mice were bled via retro-orbital puncture to prepare citrated plasma in order to determine expression levels (cfr. 3.2) up to 15 days post DNA injection.

Neurotoxicity

Neuronal cultures were prepared from Swiss mouse embryos (embryonic day 14). Cortices were dissected and dissociated in DMEM, and plated on 24-well plates coated with poly-D-lysine (0.1 mg/ml) and laminin (0.02 mg/ml). Cells were cultured in DMEM supplemented with 5% foetal bovine serum, 5% horse serum (both from Invitrogen, Cergy Pontoise, France) and 2 mM glutamine. Cultures were maintained at 37° C. in a humidified 5% $CO_2$ atmosphere. To inhibit glial proliferation, cytosine β-D-arabinoside (10 µM) was added after 3 days in vitro (DIV) to the cortical cultures.

Excitotoxicity was induced at 12-13 DIV by exposure to NMDA (10 µM) in serum-free DMEM supplemented with 10 µM of glycine for 24 hours. NMDA was applied alone or together with rtPA (20 µg/ml) and/or diabody (5 µg/ml). As a control, the diabody was added to the neuronal culture at 12-13 DIV at several concentrations (0.5 µg/ml-50 µg/ml) in the absence of NMDA. After 24 hours, neuronal death was quantified by measurement of the activity of lactate dehydrogenase (LDH) released from damaged cells into the bathing medium (Roche Diagnostics, Mannheim, Germany). The LDH level corresponding to the maximal neuronal death (full kill, FK) was determined in sister cultures exposed to 500 µM NMDA. Background LDH levels were determined in sister cultures subjected to control washes. Experimental values were measured after subtracting $LDH_{min}$ and then normalized to $LDH_{max}$-$LDH_{min}$ to express the results in percentage of neuronal death.

Statistical Analysis

All quantitative data are presented as mean and standard error of mean (SEM). Circulating half-life of the diabody was retrieved after nonlinear fitting of plasma levels plotted against time (Graphpad Prism Version 5, GraphPad Software, Inc., San Diego, Calif., USA). Statistical analysis was performed with GraphPad Prism Version 5 (GraphPad Software). Curves from thromboelastometry (retrieved from the Export tool) were integrated with GraphPad Prism 5. A chi-square test was performed to compare angiographic scores from different treatment groups. Outliers were excluded by performing the Grubb's test. Prior to statistical analysis, a D'Agostino and Pearson normality test was used to check data distribution. One-way ANOVA with Bonferroni's multiple comparison test was used for statistical comparison of lesion volumes and speckle contrast imaging data after $FeCl_3$-induced MCAo and an unpaired students t-test was used for statistical comparison of lesion volumes after mechanical tMCAo. Kruskal-Wallis ANOVA with Dunn's multiple comparison test was used for statistical comparison of: (i)) thromboelastometric parameters for lysis, Δ L and relative Δ AUC, (ii) lung fibrinogen equivalents in the venous thromboembolism model; (iii) lesion volumes and speckle contrast imaging data in the IIa-induced MCAo model; (iv) laser Doppler data in the FeCl$_3$-induced MCAo model and (v) tail bleeding times and haemoglobin contents. A Mann-Whitney test was performed for statistical analysis of neurological/motor data, fibrinogen levels after mechanical tMCAo and in vitro neurotoxicity data. P-values less than 0.05 were considered significant.

Sequences Disclosed in the Application.

Underlined text: CDR sequences

N terminal Met Ala residues in SEQ ID 17 and 18 are from the PelB signal peptide Bold text: synthetic linkers and tags

| SEQ ID NO | Description | Sequence |
| --- | --- | --- |
| SEQ ID NO: 1 | VH TCK26D6 CDR1 | DNNMD |
| SEQ ID NO: 2 | VH TCK26D6 CDR2 | SXYSNNGGTIYNQKFKG (where X may be V or I) |
| SEQ ID NO: 3 | VH TCK26D6 CDR3 | EMSDGPYWFFDV |
| SEQ ID NO: 4 | VL TCK26D6 CDR1 | RASENIFRNLV |
| SEQ ID NO: 5 | VL TCK26D6 CDR2 | SATNLVD |
| SEQ ID NO: 6 | VL TCK26D6 CDR3 | QHFWGTPRT |
| SEQ ID NO: 7 | VH 33H1F7 CDR1 | DTYIH |
| SEQ ID NO: 8 | VH 33H1F7 CDR2 | RIDPANGNTKYDSKFQD |
| SEQ ID NO: 9 | VH 33H1F7 CDR3 | GDYDYVYFDY |
| SEQ ID NO: 10 | VL 33H1F7 CDR1 | RASQDISNFLD |
| SEQ ID NO: 11 | VL 33H1F7 CDR2 | YTSRLHS |
| SEQ ID NO: 12 | VL 33H1F7 CDR3 | QQGNTFPPT |
| SEQ ID NO: 13 | VH TCK26D6 | QVQLQQSGPELVKPGASVKISCKASGYTFTDNNMDWAKQSHGKSLEWIGSXYSNNGGTIYNQKFKGKATLNVDTSSSTAYMELRSLTSEDTAVYYCAREMSDGPYWFFDVWGTGTTVTVSG (where X may be V or I) |
| SEQ ID NO: 14 | VL TCK26D6 | DIQMTQSPASLSVSVGETVTITCRASENIFRNLVWYQQKQGKSPQLLVYSATNLVDGVPSRFSGSGSGTQYSLKINSLQSEDFGSYYCQHFWGTPRTFGGGTKLEIKR |
| SEQ ID NO: 15 | VH 33H1F7 | QVQLQQSGAEVVKPGASVKLACTASGFNIKDTYIHWVKQGPEQGLEWIGRIDPANGNTKYDSKFQDKATITADTSSNTAYLHLSSLTSEDTAVYYCVRGDYDYVYFDYWGQGTTVTVSS |
| SEQ ID NO: 16 | VL 33H1F7 | DIQMTQSPSSLSASLGDRVTISCRASQDISNFLDWYQQKPDGTVKLLIYYTSRLHSGVPSRFSGSGSGTDYSLTISKLEQEDIATYFCQQGNTFPPTFGGGTLKEIKR |
| SEQ ID NO: 17 | Polypeptide 1 | MAQVQLQQSGPELVKPGASVKISCKASGYTFTDNNMDWAKQSHGKSLEWIGSIYSNNGGTIYNQKFKGKATLNVDTSSSTAYMELRSLTSEDTAVYYCAREMSDGPYWFFDVWGTGTTVTVSGAKTTPKLGGDIQMTQSPSSLSASLGDRVTISCRASQDISNFLDWYQQKPDGTVKLLIYYTSRLHSGVPSRFSGSGSGTDYSLTISKLEQEDIATYFCQQGNTFPPTFGGGTKLEIKRADAAAAGSEQKLISEEDLNSHHHHHH |
| SEQ ID NO: 18 | Polypeptide 2 | MAQVQLQQSGAEVVKPGASVKLACTASGFNIKDTYIHWVKQGPEQGLEWIGRIDPANGNTKYDSKFQDKATITADTSSNTAYLHLSSLTSEDTAVYYCVRGDYDYVYFDYWGQGTTVTVSSAKTTPKLGGDIQMTQSPASLSVSVGETVTITCRASENIFRNLV |

| SEQ ID NO | Description | Sequence |
|---|---|---|
| | | WYQQKGKSPQLLVYSATNLVDGVPSRFSGSGSGTQYSLKI NSLQSEDFGSYYCQHFWGTPRTFGGGTKLEIKRADTAPTGS EQKLISEEDLNSHHHHHH |

The invention claimed is:

1. A method of treating a patient having, or at risk of developing, an acute thrombotic disorder, said method comprising a step of administering a bispecific antibody against TAFI and PAI-1, wherein said antibody comprises:
   a. a first targeting domain that specifically binds to Thrombin Activatable Fibrinolysis Inhibitor (TAFI) and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L, and
   b. a second targeting domain that specifically binds to Plasminogen Activator Inhibitor-1 (PAI-1) and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L,
   wherein the step of administering is performed:
      (i) without administration of tPA prior to the administration of the bispecific antibody,
      (ii) without administration of tPA concurrently with the administration of the bispecific antibody, or
      (iii) without administration of tPA after the administration of the bispecific antibody.

2. The method according to claim 1, wherein
   a. said first targeting domain that binds to Thrombin Activatable Fibrinolysis Inhibitor (TAFI) comprises a VH region represented by an amino acid sequence that is at least 80% identical to SEQ ID NO:13 and a VL region represented by an amino acid sequence that is at least 80% identical to SEQ ID NO:14 and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L; and
   b. said second targeting domain that binds to Plasminogen Activator Inhibitor-1 (PAI-1) and comprises a VH region represented by an amino acid sequence that is at least 80% identical to SEQ ID NO:15 and a VL region represented by an amino acid sequence that is at least 80% identical to SEQ ID NO:16, and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L.

3. The method according to claim 1,
   wherein said first targeting domain that binds to Thrombin Activatable Fibrinolysis Inhibitor (TAFI) comprises a VH region represented by an amino acid sequence that is at least 90% identical to SEQ ID NO:13 and comprises a VL region represented by an amino acid sequence that is at least 90% identical to SEQ ID NO:14, and
   wherein said second targeting domain that binds to Plasminogen Activator Inhibitor-1(PAI-1) comprises a VH region represented by an amino acid sequence that is at least 90% identical to SEQ ID NO:15 and comprises a VL region represented by an amino acid sequence that is at least 90% identical to SEQ ID NO:16.

4. The method according to claim 1,
   wherein said first targeting domain that binds to Thrombin Activatable Fibrinolysis Inhibitor (TAFI) comprises a VH region represented by an amino acid sequence that is at least 95% identical to SEQ ID NO:13 and comprises a VL region represented by an amino acid sequence that is at least 95% identical to SEQ ID NO:14, and
   wherein said second targeting domain that binds to Plasminogen Activator Inhibitor-1(PAI-1) comprises a VH region represented by an amino acid sequence that is at least 95% identical to SEQ ID NO:15 and comprises a VL region represented by an amino acid sequence that is at least 95% identical to SEQ ID NO:16.

5. The method according to claim 1,
   wherein said first targeting domain that binds to Thrombin Activatable Fibrinolysis Inhibitor (TAFI) comprises a VH region represented by an amino acid sequence that is at least 98% identical to SEQ ID NO:13 and comprises a VL region represented by an amino acid sequence that is at least 98% identical to SEQ ID NO:14, and
   wherein said second targeting domain that binds to Plasminogen Activator Inhibitor-1 (PAI-1) comprises a VH region represented by an amino acid sequence that is at least 98% identical to SEQ ID NO:15 and comprises a VL region represented by an amino acid sequence that is at least 98% identical to SEQ ID NO:16.

6. The method according to claim 1, wherein said bispecific antibody is humanized.

7. The method according to claim 1, wherein the acute thrombotic disorder is selected from the group consisting of, acute peripheral arterial occlusion, middle cerebral artery occlusion (MCAO), and thromboembolism.

8. The method according to claim 1, wherein said acute thrombotic disorder is characterized by presence of a platelet-rich blood clot.

9. The method according to claim 1, wherein
   said first targeting domain that binds to Thrombin Activatable Fibrinolysis Inhibitor (TAFI ) comprises a VH region represented by an amino acid sequence that is at least 80% identical to SEQ ID NO:13 and a VL region represented by an amino acid sequence that is at least 80% identical to SEQ ID NO:14 and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L.

10. The method according to claim 1, wherein
said second targeting domain that binds to Plasminogen Activator Inhibitor-1 (PAI-1) and comprises a VH region represented by an amino acid sequence that is at least 80% identical to SEQ ID NO:15 and a VL region represented by an amino acid sequence that is at least 80% identical to SEQ ID NO:16, and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L.

11. The method according to claim 1,
wherein said first targeting domain that binds to Thrombin Activatable Fibrinolysis Inhibitor (TAFI) comprises a VH region represented by an amino acid sequence that is at least 90% identical to SEQ ID NO:13 and comprises a VL region represented by an amino acid sequence that is at least 90% identical to SEQ. ID NO:14.

12. The method according to claim 1, wherein
wherein said second targeting domain that binds to Plasminogen Activator Inhibitor-1(PAI-1) comprises a VH region represented by an amino acid sequence that is at least 90% identical to SEQ ID NO:15 and comprises a VL region represented by an amino acid sequence that is at least 90% identical to SEQ ID NO:16.

13. The method according to claim 1,
wherein said first targeting domain that binds to Thrombin Activatable Fibrinolysis Inhibitor (TAFI) comprises a VH region represented by an amino acid sequence that is at least 95% identical to SEQ ID NO:13 and comprises a VL region represented by an amino acid sequence that is at least 95% identical to SEQ. ID NO:14.

14. The method according to claim 1, wherein
wherein said second targeting domain that binds to Plasminogen Activator Inhibitor-1 (PAI-1) comprises a VH region represented by an amino acid sequence that is at least 95% identical to SEQ ID NO:15 and comprises a VL region represented by an amino acid sequence that is at least 95% identical to SEQ ID NO:16.

15. The method according to claim 1,
wherein said first targeting domain that binds to Thrombin Activatable Fibrinolysis Inhibitor (TAFI) comprises a VH region represented by an amino acid sequence that is at least 98% identical to SEQ ID NO:13 and comprises a VL region represented by an amino acid sequence that is at least 98% identical to SEQ. ID NO:14.

16. The method according to claim 1, wherein
wherein said second targeting domain that binds to Plasminogen Activator Inhibitor-1 (PAI-1) comprises a VH region represented by an amino acid sequence that is at least 98% identical to SEQ ID NO:15 and comprises a VL region represented by an amino acid sequence that is at least 98% identical to SEQ ID NO:16.

17. The method according to claim 1, wherein the acute thrombotic disorder includes stroke, acute ischemic stroke, and middle cerebral artery occlusion.

18. The method according to claim 1, wherein said bispecific antibody against TAFI and PAI-1 is administered as a bolus.

19. A method of treating a patient for a condition or risk of acute thrombotic disorder, said method comprising
administering a bispecific antibody against TAFI and PAI-1 to the patient, said administering being performed without administration of tPA,
wherein said bispecific antibody includes
 a. a first targeting domain that specifically binds to Thrombin Activatable Fibrinolysis Inhibitor (TAFI) and comprises complementary determining regions (CDRs) represented by the amino acid sequences SEQ ID NO:1 of CDR1H, SEQ ID NO:2 of CDR2H, SEQ ID NO:3 of CDR3H, SEQ ID NO:4 of CDR1L, SEQ ID NO:5 of CDR2L, and SEQ ID NO:6 of CDR3L, and
 b. a second targeting domain that specifically binds to Plasminogen Activator Inhibitor-1 (PAI-1) and comprises complementary determining regions (CDRs) represented by SEQ ID NO:7 of CDR1H, SEQ ID NO:8 of CDR2H, SEQ ID NO:9 of CDR3H, SEQ ID NO:10 of CDR1L, SEQ ID NO:11 of CDR2L and SEQ ID NO:12 of CDR3L.

\* \* \* \* \*

SEQUENCE LISTING

```
<160> NUMBER OF SEQ ID NOS: 18

<210> SEQ ID NO 1
<211> LENGTH: 5
<212> TYPE: PRT
<213> ORGANISM: Mus musculus

<400> SEQUENCE: 1

Asp Asn Asn Met Asp
1               5

<210> SEQ ID NO 2
<211> LENGTH: 17
<212> TYPE: PRT
<213> ORGANISM: Mus musculus
<220> FEATURE:
<221> NAME/KEY: PRT
<222> LOCATION: (2)..(2)
<223> OTHER INFORMATION: Xaa may be Val or Ile

<400> SEQUENCE: 2

Ser Xaa Tyr Ser Asn Asn Gly Gly Thr Ile Tyr Asn Gln Lys Phe Lys
1               5                   10                  15

Gly

<210> SEQ ID NO 3
<211> LENGTH: 12
<212> TYPE: PRT
<213> ORGANISM: Mus musculus

<400> SEQUENCE: 3

Glu Met Ser Asp Gly Pro Tyr Trp Phe Phe Asp Val
1               5                   10

<210> SEQ ID NO 4
<211> LENGTH: 11
<212> TYPE: PRT
<213> ORGANISM: Mus musculus

<400> SEQUENCE: 4

Arg Ala Ser Glu Asn Ile Phe Arg Asn Leu Val
1               5                   10

<210> SEQ ID NO 5
<211> LENGTH: 7
<212> TYPE: PRT
<213> ORGANISM: Mus musculus

<400> SEQUENCE: 5

Ser Ala Thr Asn Leu Val Asp
1               5

<210> SEQ ID NO 6
<211> LENGTH: 9
<212> TYPE: PRT
<213> ORGANISM: Mus musculus
```

<400> SEQUENCE: 6

Gln His Phe Trp Gly Thr Pro Arg Thr
1               5

<210> SEQ ID NO 7
<211> LENGTH: 5
<212> TYPE: PRT
<213> ORGANISM: Mus musculus

<400> SEQUENCE: 7

Asp Thr Tyr Ile His
1               5

<210> SEQ ID NO 8
<211> LENGTH: 17
<212> TYPE: PRT
<213> ORGANISM: Mus musculus

<400> SEQUENCE: 8

Arg Ile Asp Pro Ala Asn Gly Asn Thr Lys Tyr Asp Ser Lys Phe Gln
1               5                   10                  15

Asp

<210> SEQ ID NO 9
<211> LENGTH: 10
<212> TYPE: PRT
<213> ORGANISM: Mus musculus

<400> SEQUENCE: 9

Gly Asp Tyr Asp Tyr Val Tyr Phe Asp Tyr
1               5                   10

<210> SEQ ID NO 10
<211> LENGTH: 11
<212> TYPE: PRT
<213> ORGANISM: Mus musculus

<400> SEQUENCE: 10

Arg Ala Ser Gln Asp Ile Ser Asn Phe Leu Asp
1               5                   10

<210> SEQ ID NO 11
<211> LENGTH: 7
<212> TYPE: PRT
<213> ORGANISM: Mus musculus

<400> SEQUENCE: 11

Tyr Thr Ser Arg Leu His Ser
1               5

<210> SEQ ID NO 12
<211> LENGTH: 9
<212> TYPE: PRT
<213> ORGANISM: Mus musculus

<400> SEQUENCE: 12

Gln Gln Gly Asn Thr Phe Pro Pro Thr
1               5

<210> SEQ ID NO 13
<211> LENGTH: 121
<212> TYPE: PRT
<213> ORGANISM: Mus musculus

```
<220> FEATURE:
<221> NAME/KEY: PEPTIDE
<222> LOCATION: (51)..(51)
<223> OTHER INFORMATION: Xaa may be Val or Ile

<400> SEQUENCE: 13

Gln Val Gln Leu Gln Gln Ser Gly Pro Glu Leu Val Lys Pro Gly Ala
1               5                   10                  15

Ser Val Lys Ile Ser Cys Lys Ala Ser Gly Tyr Thr Phe Thr Asp Asn
            20                  25                  30

Asn Met Asp Trp Ala Lys Gln Ser His Gly Lys Ser Leu Glu Trp Ile
        35                  40                  45

Gly Ser Xaa Tyr Ser Asn Asn Gly Gly Thr Ile Tyr Asn Gln Lys Phe
    50                  55                  60

Lys Gly Lys Ala Thr Leu Asn Val Asp Thr Ser Ser Thr Ala Tyr
65                  70                  75                  80

Met Glu Leu Arg Ser Leu Thr Ser Glu Asp Thr Ala Val Tyr Tyr Cys
                85                  90                  95

Ala Arg Glu Met Ser Asp Gly Pro Tyr Trp Phe Phe Asp Val Trp Gly
            100                 105                 110

Thr Gly Thr Thr Val Thr Val Ser Gly
        115                 120

<210> SEQ ID NO 14
<211> LENGTH: 108
<212> TYPE: PRT
<213> ORGANISM: Mus musculus

<400> SEQUENCE: 14

Asp Ile Gln Met Thr Gln Ser Pro Ala Ser Leu Ser Val Ser Val Gly
1               5                   10                  15

Glu Thr Val Thr Ile Thr Cys Arg Ala Ser Glu Asn Ile Phe Arg Asn
            20                  25                  30

Leu Val Trp Tyr Gln Gln Lys Gln Gly Lys Ser Pro Gln Leu Leu Val
        35                  40                  45

Tyr Ser Ala Thr Asn Leu Val Asp Gly Val Pro Ser Arg Phe Ser Gly
    50                  55                  60

Ser Gly Ser Gly Thr Gln Tyr Ser Leu Lys Ile Asn Ser Leu Gln Ser
65                  70                  75                  80

Glu Asp Phe Gly Ser Tyr Tyr Cys Gln His Phe Trp Gly Thr Pro Arg
                85                  90                  95

Thr Phe Gly Gly Gly Thr Lys Leu Glu Ile Lys Arg
            100                 105

<210> SEQ ID NO 15
<211> LENGTH: 119
<212> TYPE: PRT
<213> ORGANISM: Mus musculus

<400> SEQUENCE: 15

Gln Val Gln Leu Gln Gln Ser Gly Ala Glu Val Val Lys Pro Gly Ala
1               5                   10                  15

Ser Val Lys Leu Ala Cys Thr Ala Ser Gly Phe Asn Ile Lys Asp Thr
            20                  25                  30

Tyr Ile His Trp Val Lys Gln Gly Pro Glu Gln Gly Leu Glu Trp Ile
        35                  40                  45

Gly Arg Ile Asp Pro Ala Asn Gly Asn Thr Lys Tyr Asp Ser Lys Phe
    50                  55                  60
```

```
Gln Asp Lys Ala Thr Ile Thr Ala Asp Thr Ser Ser Asn Thr Ala Tyr
 65                  70                  75                  80

Leu His Leu Ser Ser Leu Thr Ser Glu Asp Thr Ala Val Tyr Tyr Cys
             85                  90                  95

Val Arg Gly Asp Tyr Asp Tyr Val Tyr Phe Asp Tyr Trp Gly Gln Gly
            100                 105                 110

Thr Thr Val Thr Val Ser Ser
            115
```

<210> SEQ ID NO 16
<211> LENGTH: 108
<212> TYPE: PRT
<213> ORGANISM: Mus musculus

<400> SEQUENCE: 16

```
Asp Ile Gln Met Thr Gln Ser Pro Ser Ser Leu Ser Ala Ser Leu Gly
 1               5                  10                  15

Asp Arg Val Thr Ile Ser Cys Arg Ala Ser Gln Asp Ile Ser Asn Phe
             20                  25                  30

Leu Asp Trp Tyr Gln Gln Lys Pro Asp Gly Thr Val Lys Leu Leu Ile
         35                  40                  45

Tyr Tyr Thr Ser Arg Leu His Ser Gly Val Pro Ser Arg Phe Ser Gly
 50                  55                  60

Ser Gly Ser Gly Thr Asp Tyr Ser Leu Thr Ile Ser Lys Leu Glu Gln
 65                  70                  75                  80

Glu Asp Ile Ala Thr Tyr Phe Cys Gln Gln Gly Asn Thr Phe Pro Pro
             85                  90                  95

Thr Phe Gly Gly Gly Thr Lys Leu Glu Ile Lys Arg
            100                 105
```

<210> SEQ ID NO 17
<211> LENGTH: 266
<212> TYPE: PRT
<213> ORGANISM: Mus musculus

<400> SEQUENCE: 17

```
Met Ala Gln Val Gln Leu Gln Gln Ser Gly Pro Glu Leu Val Lys Pro
 1               5                  10                  15

Gly Ala Ser Val Lys Ile Ser Cys Lys Ala Ser Gly Tyr Thr Phe Thr
             20                  25                  30

Asp Asn Asn Met Asp Trp Ala Lys Gln Ser His Gly Lys Ser Leu Glu
         35                  40                  45

Trp Ile Gly Ser Ile Tyr Ser Asn Asn Gly Gly Thr Ile Tyr Asn Gln
 50                  55                  60

Lys Phe Lys Gly Lys Ala Thr Leu Asn Val Asp Thr Ser Ser Ser Thr
 65                  70                  75                  80

Ala Tyr Met Glu Leu Arg Ser Leu Thr Ser Glu Asp Thr Ala Val Tyr
             85                  90                  95

Tyr Cys Ala Arg Glu Met Ser Asp Gly Pro Tyr Trp Phe Phe Asp Val
            100                 105                 110

Trp Gly Thr Gly Thr Thr Val Thr Val Ser Gly Ala Lys Thr Thr Pro
            115                 120                 125

Lys Leu Gly Gly Asp Ile Gln Met Thr Gln Ser Pro Ser Ser Leu Ser
        130                 135                 140

Ala Ser Leu Gly Asp Arg Val Thr Ile Ser Cys Arg Ala Ser Gln Asp
145                 150                 155                 160
```

```
Ile Ser Asn Phe Leu Asp Trp Tyr Gln Gln Lys Pro Asp Gly Thr Val
            165                 170                 175

Lys Leu Leu Ile Tyr Tyr Thr Ser Arg Leu His Ser Gly Val Pro Ser
        180                 185                 190

Arg Phe Ser Gly Ser Gly Ser Gly Thr Asp Tyr Ser Leu Thr Ile Ser
    195                 200                 205

Lys Leu Glu Gln Glu Asp Ile Ala Thr Tyr Phe Cys Gln Gln Gly Asn
    210                 215                 220

Thr Phe Pro Pro Thr Phe Gly Gly Gly Thr Lys Leu Glu Ile Lys Arg
225                 230                 235                 240

Ala Asp Ala Ala Ala Gly Ser Glu Gln Lys Leu Ile Ser Glu Glu
            245                 250                 255

Asp Leu Asn Ser His His His His His His
            260                 265

<210> SEQ ID NO 18
<211> LENGTH: 264
<212> TYPE: PRT
<213> ORGANISM: Mus musculus

<400> SEQUENCE: 18

Met Ala Gln Val Gln Leu Gln Gln Ser Gly Ala Glu Val Val Lys Pro
1               5                   10                  15

Gly Ala Ser Val Lys Leu Ala Cys Thr Ala Ser Gly Phe Asn Ile Lys
            20                  25                  30

Asp Thr Tyr Ile His Trp Val Lys Gln Gly Pro Glu Gln Gly Leu Glu
        35                  40                  45

Trp Ile Gly Arg Ile Asp Pro Ala Asn Gly Asn Thr Lys Tyr Asp Ser
    50                  55                  60

Lys Phe Gln Asp Lys Ala Thr Ile Thr Ala Asp Thr Ser Ser Asn Thr
65                  70                  75                  80

Ala Tyr Leu His Leu Ser Ser Leu Thr Ser Glu Asp Thr Ala Val Tyr
                85                  90                  95

Tyr Cys Val Arg Gly Asp Tyr Asp Tyr Val Tyr Phe Asp Tyr Trp Gly
            100                 105                 110

Gln Gly Thr Thr Val Thr Val Ser Ser Ala Lys Thr Thr Pro Lys Leu
        115                 120                 125

Gly Gly Asp Ile Gln Met Thr Gln Ser Pro Ala Ser Leu Ser Val Ser
    130                 135                 140

Val Gly Glu Thr Val Thr Ile Thr Cys Arg Ala Ser Glu Asn Ile Phe
145                 150                 155                 160

Arg Asn Leu Val Trp Tyr Gln Gln Lys Gln Gly Lys Ser Pro Gln Leu
                165                 170                 175

Leu Val Tyr Ser Ala Thr Asn Leu Val Asp Gly Val Pro Ser Arg Phe
            180                 185                 190

Ser Gly Ser Gly Ser Gly Thr Gln Tyr Ser Leu Lys Ile Asn Ser Leu
        195                 200                 205

Gln Ser Glu Asp Phe Gly Ser Tyr Tyr Cys Gln His Phe Trp Gly Thr
    210                 215                 220

Pro Arg Thr Phe Gly Gly Gly Thr Lys Leu Glu Ile Lys Arg Ala Asp
225                 230                 235                 240
```

```
Thr Ala Pro Thr Gly Ser Glu Gln Lys Leu Ile Ser Glu Glu Asp Leu
                245                 250                 255
Asn Ser His His His His His His
            260
```